US010379118B2

(12) United States Patent
Orlova et al.

(10) Patent No.: US 10,379,118 B2
(45) Date of Patent: Aug. 13, 2019

(54) QUANTIFICATION OF ANTIGEN MOLECULES USING DYNAMIC FLOW CYTOMETRY

(71) Applicant: The Board of Trustees of the Leland Sanford Junior University, Palo Alto, CA (US)

(72) Inventors: Darya Y. Orlova, Menlo Park, CA (US); David R. Parks, San Francisco, CA (US); Leonore A. Herzenberg, Stanford, CA (US); Andrei V. Chernyshev, Novosibirsk (RU); Alexander E. Moskalensky, Novosibirsk (RU)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 461 days.

(21) Appl. No.: 15/040,631

(22) Filed: Feb. 10, 2016

(65) Prior Publication Data
US 2016/0238597 A1 Aug. 18, 2016

Related U.S. Application Data

(60) Provisional application No. 62/116,492, filed on Feb. 15, 2015.

(51) Int. Cl.
*G01N 15/14* (2006.01)
*G01N 33/557* (2006.01)
*G01N 33/49* (2006.01)

(52) U.S. Cl.
CPC ........... *G01N 33/557* (2013.01); *G01N 15/14* (2013.01); *G01N 33/4915* (2013.01); *G01N 2333/7051* (2013.01); *G01N 2333/70517* (2013.01)

(58) Field of Classification Search
CPC .. G01N 33/557; G01N 33/4915; G01N 15/14; G01N 2333/7051; G01N 2333/70571
See application file for complete search history.

(56) References Cited

U.S. PATENT DOCUMENTS 5,620,842 A 4/1997 Davis et al.
5,656,503 A 8/1997 May et al.

OTHER PUBLICATIONS

Orlova et al. Distribution function approace to the study of the kinetics of IgM antibody binding to Fc1RIIIb (CD16b) receptors on neutrophils by flow cytometry. Journal of Theoretical Biology 290: 1-6 (2011).*

Poncelet et al. Cytofluorometric Quantitation of Cell-Surface Antigens by Indirect Immunofluorescence Using Monoclonal Antibodies . Journal of Immunological Methods 85: 65-74 (1985).*
Bendall SC et al. A deep profiler's guide to cytometry. Trends in Immunology. 2012. vol. 33(7):323-32. doi: 10.1016/j.it.2012.02.010.
Perfetto SP et al. Seventeen-colour flow cytometry: Unravelling the immune system. Nature Reviews. vol. 4: 648-655. doi:10.1038/nri1416, (2004).
Gernez Y et al. Blood basophils from cystic fibrosis patients with allergic bronchopulmonary aspergillosis are primed and hyperresponsive to stimulation by aspergillus allergens. Journal of Cystic Fibrosis. 2012. vol. 11 (6):502-510. doi: 10.1016/j.jcf.2012.04.008.
Serke S et al. Expression of class I, II, and III epitopes of the CD34 antigen by normal and leukemic hemopoietic cells. Cytometry. 1996. vol. 26: 154-160.
Liu Z et al. Elevated relative fluorescence intensity of CD38 antigen expression on CD8+ T cells is a marker of poor prognosis in HIV infection: results of 6 years of follow-up. Cytometry. 1996. vol. 26:1-7.
Chance JT et al., Instrument-dependent fluorochrome sensitivity in flow cytometric analyses, Cytometry. 1995. vol. 22(3):232-42.
Serke S et al. Quantitative fluorescence flow cytometry: A comparison of the three techniques for direct and indirect immunofluorescence.,Cytometry. 1998. vol. 33(2):179-87.
Schwartz A et al. Development of clinical standards for flow cytometry. Ann N Y Acad Sci. 1993. vol. 677:28-39. doi:10.1111/j.1749-6632.1993.tb38760.x.
Poncelet P et al. Cytofluorometric quantification of cell-surface antigens by indirect immunofluorescence using monoclonal antibodies. Journal of Immunological Methods. 1985. vol. 85(1):65-74. doi:10.1016/0022-1759(85)90274-1.
Denny TN et al. Quantitative determination of surface antibody capacities of immune subset present in peripheral blood of healthy adult donors. Cytometry. 1996. vol. 26:265-274.
Lenkei R et al. Determination of the antibody binding capacity of lymphocyte membrane antigens by flow cytometry in 58 blood donors. Journal of Immunological Methods. 1995. vol. 183:267-277. doi: 10.1016/0022-1759(95)00064-H).
Orlova D et al. Distribution function approach to study the kinetics of IgM antibodies binding to Fc?RlIIb (CD16b) receptors on neutrophils by Flow Cytometry. Journal of Theoretical Biology. 2011. vol. 290:1-6. doi:10.1016/j.itbi.2011.08.026.
Surovtsev IV et al. Mathematical modeling the kinetics of cell distribution in the process of ligand-receptor binding. Journal Theoretical Biology. 2000. vol. 206(3):407-17. doi:10.1006/jtbi.2000.2136.
CD27 CD27 molecule [*Homo sapiens* (humans)]—Gene—NCBI, www.ncbi.nlm.nih.gov/gene/939; http://www.ncbi.nlm.nih.gov/gene/939; retrieved from the Internet on Nov. 30, 2017.
CD38 CD 38 molecule [*Homo sapiens* (human)—Gene—NCBI, http://www.ncbi.nlm.nih.gov/gene/952, retrieved from be Internet on Nov. 30, 2017.

(Continued)

*Primary Examiner* — Gailene Gabel
(74) *Attorney, Agent, or Firm* — McCarter & English, LLP; Beverly W. Lubit, Esq.

(57) ABSTRACT

The described invention provides a method for quantifying cellular antigens that is independent of specially prepared calibration beads and antibody reagents. The described method can be applied to both low and high affinity antibodies, under both saturating and non-saturating binding conditions.

17 Claims, 8 Drawing Sheets

(56) References Cited

OTHER PUBLICATIONS

De Waal Malefyt, Interleukin-17 Kick-Starts T Helper 1 Cell Differentiation, Immunity 31: 700-702 (2009).
Nekrasov VM et al. Brownian aggregation rate of colloid particles with several active sites. The Journal of Chemical Physics. 2014. vol. 141(6):064309. doi: 10.1063/1.4892163.
Campanelli R et al. Human CD8 co-receptor is strictly involved in MHC-peptide tetramer-TCR binding and T cell activation. International Immunology. 2002. vol. 14:39-44. doi: 10.1093/intimm/14.1.39.
Gakamsky DM et al. CD8 kinetically promotes ligand binding to the T-cell antigen receptor. Biophysical Journal. 2005. vol. 89:2121-33. doi: 10.1529/biophysj.105.061671.
Denkberg G et al. Critical role for CD8 in binding of MHC tetramers to TCR: CD8 antibodies block specific binding of human tumor-specific MHC-peptide tetramers to TCR. The Journal of Immunology. 2001. vol. 167:270-276. doi: 10.4049/jimmunol.167.1.270.
Jun Huang. A Kinetic Study of the T Cell Recognition Mechanism. PhD thesis, Georgia Institute of Technology. 2008 (159 pgs).
Ibrahim, M., et al, Determination of diffusion coefficients proteins by flow injection analysis and its application to estimation molecular masses of proteins. Instr. Sci. Technol. 26 (4), 333-341, 1998.
Xavier KA and Willson RC, Association and Dissociation Kinetics of Anti-Hen Egg Lysozyme Monoclonal Antibodies HyHEL-5 and HyHEL-10, Biophysical Journal 1998; 74: 2036-2045.
Xavier KA et al.; Association and dissociation kinetics of bobwhite quail lysozyme with monoclonal antibody HyHEL-5; Protein Eng. 1999; 12(1): 79-83.
Kaman R et al.; Diffusion-limited rates for monoclonal antibody binding to cytochrome c; Biochemistry, 31 (1992), pp. 10370-10379.
Ito W. et al.; Mutations in the Complementarity-determining Regions do not cause Differences in Free Energy during the Process of Formation of the Activated Complex between an Antibody and the Corresponding Protein Antigen; J. Mol. Biol. 248 (1995), pp. 729-732.
Wibbenmeyer JA et al.; Salt Links Dominate Affinity of Antibody HyHEL-5 for Lysozyme through Enthalpic Contributions*; The Journal of Biological Chemistry 1999; 274(38): 26838-26842.
Kam-Morgan LNW et al.; High-resolution mapping of the HyHEL-10 epitope of chicken lysozyme by site-directed mutagenesis; Proc. Natl. Acad. Sci. USA 1993; 90: 3958-3962.
Dall'Acqua W et al., Contribution of Domain Interface Residues to the Stability of Antibody CH3 Domain Homodimers; Biochemistry 1998; 37(26): 9266-9273.
Pierce MM et al., Isothermal Titration Calorimetry of Protein-Protein Interactions, Methods 1999; 19: 213-221.
Janeway, et al., Antigen receptor structure and signaling pathways; Immunobiology: The Immune System in Health and Disease. 5th edition (2001), chapter 6; paragraph below figure 6.11; accessed Dec. 7, 2018 at https://www.ncbi.nlm.nih.gov/books/NBK27130/.

* cited by examiner

QUANTIFICATION OF ANTIGEN MOLECULES USING DYNAMIC FLOW CYTOMETRY

CROSS-REFERENCE TO RELATED APPLICATIONS

This application claims the benefit of priority to U.S. provisional application 62/116,492 filed on Feb. 15, 2015, which is incorporated herein by reference.

FIELD OF INVENTION

The described invention generally relates to a method for quantifying antigen molecules using flow cytometry.

BACKGROUND OF THE INVENTION

Flow cytometry is a powerful tool for the identification of cell populations based on the expression level of target molecules on cells. In keeping with the increasing importance of flow cytometry in biology and medicine, the number and data acquisition power of flow cytometry instruments has expanded greatly in the last few years (Bendall S C et al. A deep profiler's guide to cytometry. Trends in Immunology. 2012. Vol. 33(7):323-32. doi: 10.1016/j.it.2012.02.010; Perfetto S P et al. Seventeen-colour flow cytometry: Unravelling the immune system. Nature Reviews. Vol. 4: 648-655. doi:10.1038/nri1416). Modern flow cytometry is particularly useful for disease diagnostic purposes because it enables simultaneous measurement of up to 20 markers on the inside and surface of each of a very large number of cells in a sample. In particular, differences in antigen expression on small subsets of cells may be informative relative to clinical outcomes such as drug response, disease susceptibility and prognosis. Thus, subsets of cells identified by flow cytometry are frequently compared to find such differences. Specifically, comparisons between a disease sample and control, different genetically modified organisms, or samples that have undergone stimulations provide fundamental information (Gernez Y et al. Blood basophils from cystic fibrosis patients with allergic bronchopulmonary aspergillosis are primed and hyper-responsive to stimulation by *aspergillus* allergens. Journal of Cystic Fibrosis. 2012. Vol. 11(6):502-510. doi: 10.1016/j.jcf.2012.04.008; Serke S et al. Expression of class I, II, and III epitopes of the CD34 antigen by normal and leukemic hemopoietic cells. Cytometry. 1996. Vol. 26: 154-160; Liu Z et al. Elevated relative fluorescence intensity of CD38 antigen expression on CD8+ T cells is a marker of poor prognosis in HIV infection: results of 6 years of follow-up. Cytometry. 1996. Vol. 26:1-7). Therefore, it is important to have appropriate methods to characterize these differences in a quantitative and useful way. However, while flow instrumentation has improved markedly to meet these needs, there is still a lack of appropriate methods for clinically useful quantitation of differences between subsets of cells in routine and high-throughput analyses.

Flow cytometry users operate with relative fluorescence intensity (FI) values for the cell subset of interest, which makes it almost impossible to directly compare (without normalization on shared control samples) different flow cytometers and even different experiments on the same machine. Flow cytometer settings, in terms of lasers and optical alignment, light collection, optical filters and photodetector sensitivity (Chance J T et al. Instrument-dependent fluorochrome sensitivity in flow cytometric analyses. Cytometry. 1995. Vol. 22(3):232-42) have not been successfully standardized. In addition, different dye conjugates are often available for a given antibody, antibody preparations with the same fluorochrome vary from vendor to vendor, and differences in sample processing (e.g., the incubation time) generate additional variability.

In order to overcome these difficulties, there have been various efforts to quantitate the FI of beads (or cells), that is, to estimate the number of expressed molecules. Traditional methods for estimating the number of expressed molecules on cells, based on the detection of target antigens bound with fluorescently labeled antibodies, assume that the antigen-antibody reaction reaches equilibrium, and hence, that the amount bound correctly reports the amount of antigen on the cell. However, at a minimum, a calibration procedure with carefully prepared reagents is needed to convert the intensity of the fluorescence signal to the number of target antigens (Serke S et al. Quantitative fluorescence flow cytometry: A comparison of the three techniques for direct and indirect immunofluorescence. Cytometry. 1998. Vol. 33(2):179-87). For instance, among the currently marketed technologies, there are three technologies that are well known: Quantum Simply Cellular beads (QSC) designed to bind any fluorochrome-labeled murine monoclonal antibody; Quantitative Immunofluorescence Intensity beads (QIFI kit) for indirect immunofluorescence; and the Quanti-BRITE assay (Schwartz A et al. Development of clinical standards for flow cytometry. Ann N Y Acad Sci. 1993. Vol. 677:28-39. doi:10.1111/j.1749-6632.1993.tb38760.x; Poncelet P et al. Cytofluorometric quantification of cell-surface antigens by indirect immunofluorescence using monoclonal antibodies. Journal of Immunological Methods. 1985. Vol. 85(1):65-74. doi:10.1016/0022-1759(85)90274-1; Davis K A et al. Determination of the number of fluorescent molecules on calibration beads for flow cytometry. U.S. Pat. No. 5,620,842 A. 1997). Although the calibration bead-based technologies seem to be a straightforward and easy-to-use approach for quantitative fluorescence flow cytometry, comparison of these three technologies has revealed their limitations (Serke S et al. Quantitative fluorescence flow cytometry: A comparison of the three techniques for direct and indirect immunofluorescence. Cytometry. 1998. Vol. 33(2):179-87).

The QSC bead-based data were found to be comparable only if they were obtained using a single strictly uniform approach (Denny T N et al. Quantitative determination of surface antibody capacities of immune subset present in peripheral blood of healthy adult donors. Cytometry. 1996. Vol. 26:265-274; Lenkei R et al. Determination of the antibody binding capacity of lymphocyte membrane antigens by flow cytometry in 58 blood donors. Journal of Immunological Methods. 1995. Vol. 183:267-277. doi: 10.1016/0022-1759(95)00064-H). Additionally, the use of the QSC assay with FITC and PE reagents revealed substantially different estimates of cellular binding sites (Serke S et al. Quantitative fluorescence flow cytometry: A comparison of the three techniques for direct and indirect immunofluorescence. Cytometry. 1998. Vol. 33(2):179-87). The use of QIFI calibration kit is restricted since it is marketed with a single manufacturer-defined fluorescent antibody. The Quanti-BRITE assay is specified for use of specially-prepared equimolar (1 antibody molecule:1 PE molecule) reagents only. In general, these approaches are not applicable to labeling with lower affinity antibodies and/or to labeling under non-equilibrium conditions. The choice of calibrator, fluorochrome conjugates and details of sample handling can affect the determination of antigen concentration on beads or cells.

If target sites are very mobile (the surface diffusion of the sites on the cell membrane is fast in comparison with the 3-dimension diffusion of the ligand molecules in the medium) or sufficiently close to each other (the distance between sites are equal or less than the radius of the sites) for some IgG antibodies to bind divalently, the number of effective antibody binding sites will be lower than the number of target antigens. This is a common limitation of the antibody-based methods mentioned above. Thus, special approaches like use on univalent antibodies are needed to resolve this issue.

It has been shown that flow cytometry data for antigen-antibody interactions can be analyzed as a temporal evolution of the cellular fluorescence profile to obtain information on the cellular distribution of the surface antigens, as well as the association and dissociation rate constants per antigen (Orlova D et al. Distribution function approach to study the kinetics of IgM antibodies binding to FcγRIIIb (CD16b) receptors on neutrophils by Flow Cytometry. Journal of Theoretical Biology. 2011. Vol. 290:1-6. doi:10.1016/j.jtbi.2011.08.026; Surovtsev I V et al. Mathematical modeling the kinetics of cell distribution in the process of ligand-receptor binding. Journal Theoretical Biology. 2000. Vol. 206(3):407-17. doi:10.1006/jtbi.2000.2136). However, this information was obtained with the use of calibrators.

The described invention provides a further developed and optimized kinetic approach to antigen quantification on beads and cells which can be applied to both low and high affinity antibodies, under both saturating and non-saturating binding conditions, independent of the conjugated fluorochrome. Instead of using a static calibration system, the mean fluorescence dynamics of a population of interest measured by flow cytometry only are analyzed, in order to evaluate the amount of surface antigens. Experimental data obtained with an LSRII cytometer was fitted by the diffusion-reaction mathematical model for stable binding conditions (the solution for the general case, applied to both low and high affinity antibodies, was described in Orlova D et al. Distribution function approach to study the kinetics of IgM antibodies binding to FcγRIIIb (CD16b) receptors on neutrophils by Flow Cytometry. Journal of Theoretical Biology. 2011. Vol. 290:1-6. doi:10.1016/j.jtbi.2011.08.026) using the Levenberg-Marquardt nonlinear least squares curve-fitting algorithm in order to obtain the number of target antigens per bead/cell. As a result, the binding rate constant for each particular antibody-antigen reaction can be used instead of calibrators in order to quantify antigen molecules per cell using flow cytometry.

SUMMARY OF THE INVENTION

The described invention provides methods, compositions and kits useful to quantify antigens by flow cytometry without the use of calibrators.

According to one aspect, the described invention provides a method for quantifying a cellular antigen using flow cytometry without calibration beads, comprising: (a) isolating cells from a subject; (b) measuring concentration of the isolated cells; (c) mixing the isolated cells with a fluorescently-labeled antibody that specifically binds to an antigen expressed by the isolated cells to initiate an antibody-antigen binding reaction; (d) collecting samples of the antibody-antigen binding reaction at multiple time intervals; (e) stopping the antibody-antigen binding reaction in the collected samples; (f) analyzing the samples by flow cytometry of (e) and obtaining a measured time-series of mean fluorescence intensity (MFI); calculating reaction rate constant $k+$ for the antibody-antigen binding reaction based on the measured time-series of mean fluorescence intensity (MFI); and calculating amount of antigen n from $k+$.

According to one embodiment, the subject is a human.

According to one embodiment, the cells are selected from the consisting of cytotoxic T-cells, stem cells, granulocytes, monocytes, T-lymphocytes, B-lymphocytes, thrombocytes and natural killer cells. According to another embodiment, wherein the T-lymphocytes are selected from the group consisting of cytotoxic T-cells and helper T-cells. According to another embodiment, the T-lymphocytes are cytotoxic T-cells.

According to one embodiment, the measuring of (b) is performed by a cytometer with volumetric sample delivery. According to another embodiment, the measuring of (b) is performed by a flow cytometer.

According to one embodiment, the fluorescently-labeled antibody is a low-affinity antibody. According to another embodiment, the fluorescently-labeled antibody is a high-affinity antibody. According to another embodiment, the fluorescently-labeled antibody is a PE-labeled anti-CD8α antibody. According to another embodiment, the fluorescently-labeled antibody is a FITC-labeled anti-CD3 antibody.

According to one embodiment, the stopping of (e) is performed by the addition of phosphate buffered saline (PBS) to the collected samples.

According to one embodiment, the method further comprises calculating fluorescence signal per antibody molecule $\alpha$ from $k_+$. According to another embodiment, the method further comprises calculating antibody concentration $a_0$ from $k_+$.

According to one embodiment, the antibody-antigen binding reaction occurs under saturating binding conditions. According to another embodiment, the antibody-antigen binding reaction occurs under non-saturating binding conditions.

DETAILED DESCRIPTION OF THE INVENTION

Figure 1:
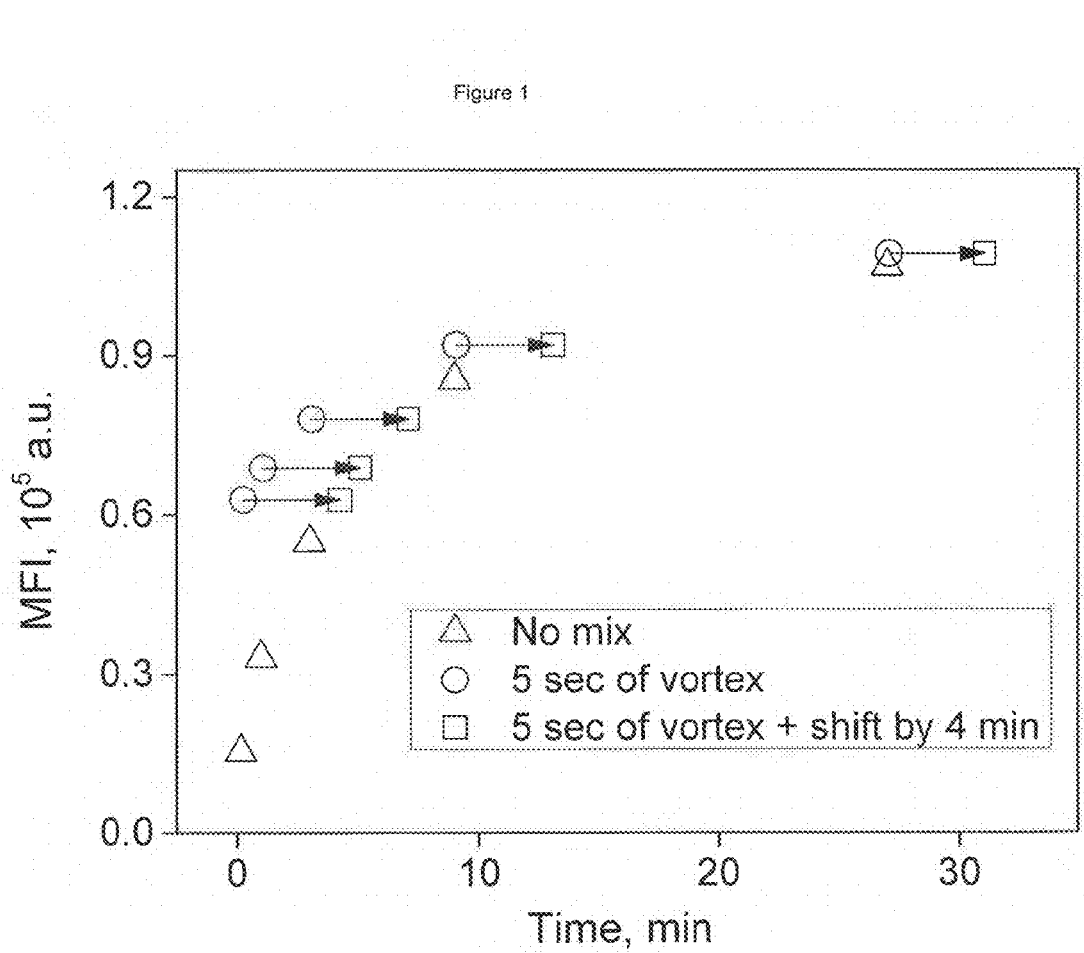
FIG. 1 depicts an example of mean fluorescence intensity (MFI) kinetics for Anti-Mouse Ig kappa microbeads binding IgG mouse monoclonal antibody (described in Sec. 2.1, 2.3). Time-series of MFI measured with and without additional mixing. Arrows represent time shift of 4 min.

The described invention can be better understood from the following description of exemplary embodiments, taken in conjunction with the accompanying figures and drawings. It should be apparent to those skilled in the art that the described embodiments of the present invention provided herein are merely exemplary and illustrative and not limiting.

Definitions

Various terms used throughout this specification shall have the definitions set out herein.

The symbol "$A_0$" as used herein, represents total concentration of antibody.

The symbol "$a_0$" as used herein, represents antibody concentration.

The symbol "$\alpha$" as used herein, represents signal per antibody molecule.

The symbol "c" as used herein, represents concentration of particles (e.g., beads, cells, etc.).

The symbol "$k_+$" as used herein, represents reaction rate constant.

The symbol "$k_+$" as used herein, represents reaction rate constant ($k_+$) multiplied by number of particles (c).

The symbol "n" as used herein, represents number of binding sites or amount of antigen per bead, per cell, etc.

The symbol "$t_0$" as used herein, represents a time shift parameter which accounts for the difference between apparent and actual starting times of antibody-antigen binding due to accelerated binding reaction between antibody and antigen after initial mixing but before the first measured time point.

The symbol "$v_1$" as used herein, represents volume of labeled antibody.

The symbol "$v_2$" as used herein, represents volume of bead suspension or volume of cell suspension.

The term "activation marker" as used herein, refers to an intracellular or cell surface marker that is highly associated with a particular cell and is selectively upregulated during a physiological condition. The physiological condition may be exposure to a substance, an allergen, a drug, a protein or a chemical, or other stimuli, or removal of a stimuli, a substance, a protein, an allergen, a drug or a chemical.

The term "affinity" as used herein, refers to a thermodynamic expression of the strength of interaction between a single antigen binding site and a single antigenic determinant (e.g., antibody and antigen). Affinity is expressed as the association constant, K. The term "high affinity" as used herein, refers to a strong intermolecular force of attraction (i.e., high/strong binding). The term "low affinity" as used herein, refers to a weak intermolecular force of attraction (i.e., low/weak binding).

The term "antigen" and its various grammatical forms refers to any substance that can stimulate the production of antibodies and/or can combine specifically with them. The term "antigenic determinant" or "epitope" as used herein refers to an antigenic site on a molecule.

The term "autologous" as used herein, means derived from the same organism.

Antibodies:

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens. The term "cross-reactivity" as used herein refers to situations in which antigenic determinants of two different antigens have some structural similarity, as a result of which some degree of fitting of one determinant into the combining site of some antibodies to the other may occur.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

The term "biomarkers" (or "biosignatures") as used herein, refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "pre B lymphocyte" refers to an early B lymphoid type cell that is recognized by immunofluorescence as a μ positive, L chain negative bone marrow cell.

The term "B lymphocyte" or "B cell" refers to a short lived immunologically important lymphocyte that is not thymus dependent and is involved in humoral immunity. It expresses immunoglobulins on its surface but does not release them. A mature B lymphocyte can be activated by the binding of an antigen to cell surface receptors, which induces proliferation of the cell, resulting in a clone of cells specific for that antigen. With interaction with helper T lymphocytes, these cells then can differentiate to mature plasma cells, which secrete immunoglobulin molecules.

The term "cytokine" as used herein, refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("ILA"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "cell surface marker" as used herein, refers to an antigenic determinant or epitope found on the surface of a specific type of cell. Cell surface markers can facilitate the characterization of a cell type, its identification, and its isolation. Cell sorting techniques are based on cellular biomarkers where a cell surface marker(s) may be used for either positive selection or negative selection, i.e., for inclusion or exclusion, from a cell population.

Cluster of Differentiation

The cluster of differentiation (CD) system is a protocol used for the identification of cell surface molecules present on white blood cells. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses ("+") or lacks ("−") a CD molecule. For example, a "CD34+, CD31−" cell is one that expresses CD34, but not CD31. Table 1 shows commonly used markers employed by skilled artisans to identify and characterize differentiated white blood cell types:

| Type of Cell | CD Markers |
| --- | --- |
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or |
|  | CD45+, CD20+ |
| Thrombocyte | CD45+, CD61+ |
| Natural killer cell | CD16+, CD56+, CD3− |

CD molecules used in defining leukocytes are not exclusively markers on the cell surface. Most CD molecules have an important function, although only a small portion of known CD molecules have been characterized. For example, there are over 350 CD for humans identified thus far.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

CD8 is a type I, disulfide-linked, heterodimeric transmembrane protein comprised of 32-34 kD monomers. CD8 is a marker for T-cells with suppressor and cytotoxic activity. It is a co-receptor with class I major histocompatibility complex (MHC-1) antigens on antigen-presenting cells, and is physically associated with a p56 tyrosine kinase which phosphorylates adjacent proteins. CD8 also may be weakly expressed by natural killer (NK) cells.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases (See, https://www.beckmancoulter.com/wsrportal/wsrportal.portal?_nfpb=true&_windowLabel=UCM_RENDERER&_urlType=render&w1pUCM_RENDERER_path=%2Fwsr%2Fresearch-and-discovery%2Fproducts-and-services%2Fflow-cytometry%2Fb-cells%2Findex.htm).

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD27 normally is found on most peripheral blood T lymphocytes, medullary thymocytes and a subpopulation of circulating B lymphocytes. CD27 is a member of the TNF-receptor superfamily. This receptor is required for the generation and maintenance of T cell immunity. CD27 binds CD70 and plays a key role in regulating B cell activation and immunoglobulin synthesis. CD27 transduces signals that lead to the activation of NF-kappaB and MAPK8/JNK (See, http://www.ncbi.nlm.nih.gov/gene/939 and http://www.bd-biosciences.com/ptProduct.jsp?prodId=22387).

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD38 is a multifunctional ectoenzyme expressed on hematopoietic cells, B cells, T cells, Natural Killer cells, monocytes and macrophages. CD38 functions in cell adhesion, signal transduction and calcium signaling (See, http://www.ncbi.nlm.nih.gov/gene/952).

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigent receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells (See, https://www.beckmancoulter.com/wsrportal/wsrportal. portal?_nfpb=true&_windowLabel=UCM RENDERER&_urlType=render&w1pUCM_RENDERER_path=%2Fwsr%2Fresearch-and-discovery%2Fproducts-and-services%2Fflow-cytometry%2Fb-cells%2Findex.htm).

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glycosylphopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronection type III (FNIII) domains being involved in signaling leading to neurite outgrowth.

CD66b ((CGM1); CD67, CGM6, NCA-95) is a glycosylphosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

CD61 (integrin (3; platelet glycoprotein Ma; ITGB3) is a cell surface protein composed of an α-chain and a β-chain. A given chain may combine with multiple partners resulting in different integrins. CD61 is found along with the α IIb chain in platelets and is known to participate in cell adhesion and cell-surface mediated signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD123 is the 70 kD transmembrane a chain of the cytokine interleukin-3 (IL-3) receptor. Alone, CD123 binds IL-3 with low affinity; when CD123 associates with CDw131 (common β chain), it binds IL-3 with high affinity. CD123 does not transduce intracellular signals upon binding IL-3 and requires the β chain for this function. CD123 is expressed by myeloid precursors, macrophages, dendritic cells, mast cells, basophils, megakaryocytes, and some B cells CD123 induces tyrosine phosphorylation within the cell and promotes proliferation and differentiation within the hematopoietic cell lines.

CD294 (G protein-coupled receptor 44; GPR44; CRTh2; DP2) is an integral membrane protein. This chemoattractant receptor homologous molecule is expressed on T helper type-2 cells. The transmembrane domains of these proteins mediate signals to the interior of the cell by activation of heterotrimeric G proteins that in turn activate various effector proteins that ultimately result a physiologic response.

The term "cytometry" as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells (or other small particles) with measured characteristics that fall within a user-selected range of values.

The term "differential label" as used herein, generally refers to a stain, dye, marker, antibody or antibody-dye combination, or intrinsically fluorescent cell-associated molecule, used to characterize or contrast components, small molecules, macromolecules, e.g., proteins, and other structures of a single cell or organism. The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyanl, Y77W, S65A, S65C, S65L, S65T, ZsGreenl, ZsYellowl, DsRed2, DsRed monomer, AsRed2, mRFP1, HcRedl, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X¬rhodamine, Lissamine Rhodamine B, Texas Red, TruRed, and derivatives thereof.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

FACS

The term "fluorescence-activated cell sorting" (also referred to as "FACS"), as used herein, refers to a method for sorting a heterogeneous mixture of biological cells into one or more containers, one cell at a time, based upon the specific light scattering and fluorescent characteristics of each cell.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

The terms "forward light scatter", "forward light scattering", "forward scatter", "forward-angle light scatter", "FSC" and "FALS" are used interchangeably herein to refer to light scattered by a particle, cell, etc., in flow cytometry in which the detector is 180°, or directly in front of, the laser beam. By way of example, in flow cytometry, when a cell passes through the laser, light is refracted in all directions, but the light that is refracted in the forward direction (i.e., along the same axis that the laser is traveling) will reach the detector.

The term "major histocompatibility complex" (MHC) as used herein, refers to a group of linked loci, collectively termed H-2 complex in the mouse and HLA complex in humans, that codes for cell-surface histocompatibility antigens and is the principal determinant of tissue type and transplant compatibility.

The term "minor histocompatibility complex" as used herein, refers to genes outside of MHC that are present on various chromosomes that encode antigens contributing to graft rejection.

The term "human leukocyte antigen (HLA)-DR" as used herein, refers to a major histocompatibility complex (MHC) class II cell surface receptor. HLA-DR commonly is found on antigen-presenting cells such as macrophages, B-cells, and dendritic cells. This cell surface molecule is a $\alpha\beta$ heterodimer with each subunit containing 2 extracellular domains: a membrane spanning domain and a cytoplasmic tail. Both the $\alpha$ and $\beta$ chains are anchored in the membrane. The complex of HLA-DR and its ligand (a peptide of at least 9 amino acids) constitutes a ligand for the TCR.

The term "integrins" as used herein, refers to receptors that mediate attachment between a cell and the tissues surrounding it and are involved in cell-cell and cell-matrix interactions. In mammals, 18$\alpha$ and 8$\beta$ subunits have been characterized. Both $\alpha$ and $\beta$ subunits contain two separate tails, both of which penetrate the plasma membrane and possess small cytoplasmic domains.

Integrin $\alpha$M (ITGAM; CD11b); macrophage-1 antigen (Mac-1); complement receptor 3 (CR3)) is a protein subunit of the heterodimeric integrin $\alpha$M$\beta$2 molecule. The second chain of $\alpha$M$\beta$2 is the common integrin $\beta$2 subunit (CD18). $\alpha$M$\beta$2 is expressed on the surface of many leukocytes including monocytes, granulocytes, macrophages and natural killer cells. It generally is believed that $\alpha$M$\beta$2 mediates inflammation by regulating leukocyte adhesion and migration. Further, $\alpha$M$\beta$2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin $\alpha$M$\beta$2 is involved directly in causing the adhesion and spreading of cells, but cannot mediate cellular migration without the presence of the $\beta$2 (CD18) subunit.

The term "labeling" as used herein, refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "lymphocyte" refers to a white blood cell formed in lymphatic tissue throughout the body and in normal adults making up about 22-28% of the total number of leukocytes in the circulating blood. Lymphocytes are divided into two principal groups, termed B lymphocytes and T lymphocytes, based on their surface molecules and function.

Lymphocyte activation refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. The soluble product of an activated B lymphocyte is immmunoglobulins (antibodies). The soluble product of an activated T lymphocyte is a lymphokine.

The term "mean fluorescence intensity" or "MFI" as used herein, refers to the average fluorescent intensity reading in a selected fluorescence channel (e.g., FITC, PE, PerCP, etc.). MFI is useful for detecting, for example, a shift in fluorescence intensity of a population of cells.

The terms "peripheral blood mononuclear cells" or "PBMCs" are used interchangeably herein to refer to blood cells having a single round nucleus such as, for example, a lymphocyte or a monocyte. PBMCs are a critical component in the immune system's responses to infections.

Methods for isolating PBMCs are well-known in the art. Those skilled in the art appreciate that there are many established protocols for isolating PBMCs from peripheral blood. Peripheral blood may be drawn conveniently via venipuncture. Isolation of PBMCs may include, but are not limited to, cell elutriation and density-gradient separation protocols. Exemplary density-gradient separation protocols employ, for example, Ficoll®. Briefly, blood samples may be collected in sodium heparin tubes (BD Biosciences, San Jose, Calif., Catalog No. 367874 or equivalent). Blood may be transferred to 50 mL conical tubes containing 15 mL of Ficoll®-Paque PLUS (GE Healthcare, Waukesha, Wis., Catalog No. 17-1440-03) and centrifuged at 800 rcf (1,900-2,000 rpm) for 20 minutes with centrifuge break off. After centrifugation, the buffy coat layer (containing PBMCs) may be removed and transferred to a new 50 mL conical tube. Phosphate-buffered saline (PBS) without calcium and magnesium (Gibco, Life Technologies, Carlsbad, Calif., Catalog No. 10010-023 or equivalent) may be added to the buffy coat layer so that the total volume in the conical tube is equal to 50 mL. The buffy coat layer in PBS may be centrifuged at 250 rcf (1,200 rpm) for 10 minutes with centrifuge break applied. After centrifugation, the PBS may be aspirated and the PBMC pellet may be resuspended in 48 mL of PBS. PBMCs resuspended in PBS may be centrifuged at 250 rcf (1,200 rpm) for 10 minutes with centrifuge break applied. PBS may be aspirated and PBMC pellet resuspended in 12.5% Human Serum Albumin (HSA) (Gemini Bio-Products, West Sacramento, Calif., Catalog No. 800-120 or equivalent) in RPMI medium (Sigma-Aldrich, St. Louis, Mo., Catalog No. R7388 or equivalent).

It is understood that PBMCs may be analyzed after isolation or cryopreserved for subsequent analysis. Those skilled in the art appreciate that there are many established protocols for cryopreservation of PBMCs. For example, 2× freezing media (10% HSA, Gemini Bio-Products, West Sacramento, Calif., Catalog No. 800-120 or equivalent; 20% Dimethylsulfoxide (DMSO), Sigma-Aldrich, St. Louis, Mo., Catalog No. D2650 or equivalent; RPMI medium, Sigma-Aldrich, St. Louis, Mo., Catalog No. R7388 or equivalent) chilled to 4° C. may be added dropwise to isolated PBMCs at $1 \times 10^7$ viable cells/mL in 12.5% Human Serum Albumin (HSA) (Gemini Bio-Products, West Sacramento, Calif., Catalog No. 800-120 or equivalent) in RPMI medium (Sigma-Aldrich, St. Louis, Mo., Catalog No. R7388 or equivalent) until the freezing media contains a final concentration of 5% HSA, 10% DMSO in RPMI medium. PBMCs in freezing media may be aliquoted into cryovials (Nunc, Thermo Scientific, Waltham, Mass., Catalog No. 12-565-297 or equivalent) (1 mL/cryovial) and placed on ice. Cryovials containing 1 mL of PBMCs in freezing media may be placed in a pre-cooled freezing container (Nalgene, Thermo Scientific, Waltham, Mass., Catalog No. 15-350-50 or equivalent) filled with 70% ethanol (Sigma-Aldrich, St. Louis, Mo., Catalog No. 02877 or equivalent). The freezing container may be placed at −80° C. for 24 hours before cryovials may be transferred to liquid nitrogen.

The terms "side light scatter", "side light scattering", "side scatter", "side-angle light scatter", "SSC" and "SALS" are used interchangeably herein to refer to light scattered by a particle, cell, etc., in flow cytometry in which the detector is orthogonal to the incident laser beam. Side-scattered light is proportional to the overall size of a cell but is also affected by physical characteristics including, but not limited to, internal complexity of a cell or smoothness of a cell's membrane. By way of example, a rough cell (e.g., a cell undergoing apoptosis) or a cell with great internal complexity (e.g., an eosinophil with many granuoles) would produce high side scatter signals.

The terms "saturate", "saturation conditions" and "saturated conditions" are used interchangeably herein to refer to conditions in which impregnation of one substance by another to the greatest possible extent occurs. For example, filling of all available binding sites on an antibody molecule by its antigen. The terms "non-saturate", "non-saturation conditions" and "non-saturated conditions" are used interchangeably herein to refer to conditions in which impregnation of one substance by another occurs to an extent less than the greatest possible extent. For example, not all available binding sites on an antibody are filled by its antigen.

The term "stain" as used herein, refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The term "subject" or "individual" or "patient" are used interchangeably to refer to a member of an animal species of mammalian origin, including but not limited to, mouse, rat, cat, goat, sheep, horse, hamster, ferret, pig, dog, platypus, guinea pig, rabbit and a primate, such as, for example, a monkey, ape, or human.

The T-Cell Compartment Comprises Distinct T-Cell Subsets:

The term "T lymphocyte" or "T-cell" generally refers to a thymocyte derived lymphocyte of immunologic importance that is long lived and is responsible for cell mediated immunity. Cellular immunity, the domain of T lymphocytes, is responsible for many immune reactions and is a major element in many autoimmune reactions. T-cells are known to directly kill target cells, to provide "help" for such killers, to activate other immune system cells (e.g., macrophages), to help B-cells make an antibody response, to down-modulate the activities of various immune system cells, and to secrete cytokines, chemokines, and other mediators.

The type 1 and type 2 helper classes are defined by their cytokine secretion profiles. T-helper 1 (Th1) cells, which are implicated in the stimulation of inflammation, produce IFN-gamma, GM-CSF, TNF-beta, and TNFα. TNF and IFN-gamma signals synergize in inducing an activated state in the macrophage, and lead to increased expression of adhesion and homing molecules in the vascular endothelium, which recruit additional blood-born leukocytes to the site of inflammation. (Paul, Fundamentals of Immunol. p. 397). T-helper 2 (Th-2) cells produce IL-4, IL-5, IL-10, and IL-13, and provide help for B cells in their activation and differentiation leading to the humoral immune response. (de Waal Malefyt, Immunity 31: 700-702 (2009)).

Regulatory T-cells, either natural, induced, or Tr1 cells, produce IL-10 and TGFβ, suppress the activation of effector T cells, and provide a counter-balance against uncontrolled and harmful T cell responses. Id. Th9 cells may provide additional help for mast cells through the production of IL-9. Id. Th17, an additional T-cell subset, produces IL-17A, 17-17F, IL-22 and CCL20, which act on stromal and epithelial cells to induce a number of secondary effector molecules, such as G-CSF, which stimulates the production and mobilization of neutrophils, acute phase proteins, chemokines, and antimicrobial peptides. Id.

Naive T-cells can differentiate into any of the distinct T-cell subsets when activated in the presence of appropriate signals and cytokines. The induction of a maturation process in dendritic cells is a crucial step for efficient priming of naive T-cells. There is an extensive cross-regulation between subsets to ensure that the appropriate T-cell subset is activated. Id.

The described invention provides methods useful for quantifying the number of antigen molecules by flow cytometry independent of specially prepared calibration beads and antibody reagents. The methods can be applied to both low and high affinity antibodies, under both saturating and non-saturating binding conditions.

According to one embodiment, the described invention provides the use of flow cytometry. Flow cytometry is a technique for counting and examining small particles such as cells by suspending them in a stream of fluid and passing them by an electronic detection apparatus. Flow cytometry allows simultaneous multiparametric analysis of the physical and/or chemical characteristics of each individual particle or cell. Measurable physical and/or chemical characteristics include, but are not limited to, cell pigments (e.g., chlorophyll and phycoerythrin (PE)), total DNA content, total RNA content, DNA copy number variation, chromosome analysis and sorting, protein expression, localization and modification (e.g., phosphorylation), cell surface antigens (e.g., cluster of differentiation (CD) markers), intracellular antigens, nuclear antigens, enzymatic activity, apoptosis, cell viability, cell adherence (e.g., pathogen-host interaction) and the like.

Briefly, a beam of light (e.g., laser light) of a single wavelength is directed onto a hydrodynamically-focused stream of fluid. A number of detectors are aimed at the point where the stream passes through the light beam; one detector in line with the light beam (i.e., forward scatter), several detectors in perpendicular position (i.e., side scatter) and at least one fluorescence detector. Each suspended cell passing through the light beam scatters the light in some way, and fluorescent molecules (i.e., fluorophores) (e.g., naturally occurring or attached label or dye) may be excited into emitting light at a longer wavelength than the light source. The combination of scattered and fluorescent light is recorded by the detectors. The forward scatter correlates with the cell volume, while the side scatter depends upon the inner complexity of the cell (e.g., shape of the nucleus).

One skilled in the art recognizes that a binding agent may be conjugated to a compound that is useful, for example, in cell separation, therapeutic or diagnostic applications employing flow cytometry. Examples of binding agents include, but are not limited to, antibodies, avidin and streptavidin. By way of non-limiting example, a binding agent may be conjugated to a label. The label may be any entity, the presence of which can be readily detected. The label may include, but is not limited to, a direct label, such as those described in detail in May et al., U.S. Pat. No. 5,656,503. Direct labels are entities which, in their natural state, are readily visible either to the naked eye, or with the aid of an optical filter and/or applied stimulation (e.g., laser light) to promote fluorescence. Non-limiting examples of direct labels include radioactive, chemiluminescent, electroactive (e.g., redox labels) and fluorescent (i.e., fluorophore) compounds. Non-limiting examples of fluorophores include Pacific Blue™, Alexa Fluor® 405, Pacific Orange™, Qdot® 525, Qdot® 565, Qdot® 605, Qdot® 655, Qdot® 705, Qdot® 800, Alexa Fluor® 488, RPE (R-Phycoerythrin), RPE Texas Red®, RPE-Alexa Fluor® 610, TRI-COLOR®, RPE-Alexa Fluor® 700, RPE-Cy® 5.5, RPE-Cy® 7, Alexa Fluor® 647, Alexa Fluor® 700, APC-Alexa Fluor® 750 and the like. A binding agent may also be conjugated to, for example, a direct particulate label, such as a dye, metallic (e.g., gold) and colored latex particle. A binding agent may also be conjugated to, for example, a solid support including, but not limited to, a magnetic bead.

Conjugation of a label to a binding agent may be accomplished by covalent or non-covalent (including hydrophobic) bonding, or by adsorption. Techniques for conjugation are well-known in the art and may be readily adapted for the particular reagents employed.

The data generated by flow cytometers may be plotted in a single dimension to produce a histogram or in two-dimensional or three-dimensional plots. The regions on these plots may be sequentially separated, for example, based on fluorescence intensity, by creating a series of subset extractions termed "gates." One skilled in the art recognizes that specific gating protocols exist for diagnostic and clinical purposes, including, but not limited to, classification of immune system cells. By way of example, and without limitation, one skilled in the art would recognize that it is possible to define a light scattering gate to include only B lymphocytes by placing upper and lower limits on the forward and side scatter distributions.

Flow cytometers may use either light scattering in combination with fluorescence or light scattering only for analysis. Flow cytometers are available from a variety of commercial sources, including BD Biosciences (San Jose, Calif.), EMD Millipore (Billerica, Mass.), Life Technologies (Carlsbad, Calif.), Agilent (Santa Clara, Calif.), Miltenyi Biotec (Cambridge, Mass.) and the like.

It is understood that the described invention contemplates several specialized types of flow cytometry well-known in the art. Non-limiting examples include fluorescence-activated cell sorting (FACS®), magnetic-activated cell sorting (MACS®) and high-dimensional flow cytometry.

FACS provides a method of sorting a heterogeneous mixture of cells into two or more containers, a single cell at a time, based upon the specific light scattering and fluorescent characteristics of each cell. The use of multicolor, multiparameter FACS may employ primary conjugated binding agents (e.g., antibodies) at defined fluorophore-to-protein ratios. For example, the following protocol may be used to perform FACS to detect antigen-specific B lymphocytes. PBMCs may be prepared in RPMI medium containing 4% Fetal Calf Serum (FCS) (Gibco, Life Technologies, Carlsbad, Calif., Catalog No. 26010-074 or equivalent) and labeled for 15-30 minutes at 4° C. with a combination of fluorophore-conjugated monoclonal antibodies (mAbs), such as APC-CD19 mAb (BD Biosciences, San Jose, Calif., Clone HIB19, No. 561742 or equivalent), Pacific Blue™-CD27 mAb (BioLegend, San Diego, Calif., Clone 0323, No. 302821 or equivalent), PerCP Cy5.5-IgM mAb (BD Biosciences, San Jose, Calif., Clone G20-127, No. 561285 or equivalent), FITC-Igλ mAb (BD Biosciences, San Jose, Calif., Clone JDC-12, No. 562053 or equivalent) and PE-Igλ mAb (BD Biosciences, San Jose, Calif., Clone G20-193, No. 562052 or equivalent). A 1:50 dilution for specific antibodies, and 1:200 dilution for IgM and IgG controls may be used. The samples may be analyzed by a FACSAria™ II (BD Biosciences, San Jose, Calif.).

MACS provides a cell separation technique in which cells that express a specific surface antigen may be isolated from a heterogeneous mixture of cells using magnetic particles coated with a binding agent (e.g., antibody) that recognizes the specific surface antigen. For example, in a positive cell selection MACS technique, cells expressing the specific surface antigen bind to the magnetic particles. After incubation with the magnetic particles, the heterogeneous mixture of cells is transferred to a column placed in a magnetic field. The magnetic field captures the magnetic particles (including magnetic particles bound to cells expressing the specific surface antigen) while cells not expressing the specific surface antigen (i.e., not bound to magnetic particles) may be eluted as flow through. For example, positive selection involves isolation of cells (e.g., B lymphocytes) expressing a specific surface antigen (e.g., CD19) from a heterogeneous mixture of cells by binding the cells expressing the specific surface antigen to magnetic particles coated with a binding agent (e.g., antibody) that recognizes the specific surface antigen.

It is understood by those in the art that MACS also provides negative selection of cells. Negative selection, for example, involves the isolation and removal of undesired cells expressing a specific surface antigen from a heterogeneous mixture of cells by binding the cells expressing the specific surface antigen to magnetic particles coated with a binding agent (e.g., antibody) that recognizes the specific surface antigen. A magnetic field captures the magnetic particles (including magnetic particles bound to undesired cells expressing the specific surface antigen) while cells not expressing the specific surface antigen (i.e., not bound to magnetic particles) may be eluted and collected.

One skilled in the art recognizes that various MACS products are commercially available. These products include, but are not limited to, MACS microbeads (Miltenyi Biotec, Cambridge, Mass.), autoMACS® columns (Miltenyi Biotec, Cambridge, Mass.), autoMACS Pro Separator Instrument (Miltenyi Biotec, Cambridge, Mass.), and the like.

High-dimensional flow cytometry provides a method of sorting a heterogeneous mixture of cells into two or more containers, a single cell at a time, using 6-12 fluorescent colors (i.e., fluorophores). For example, the following protocol may be used to perform FACS to detect antigen-specific B lymphocytes. Cryopreserved peripheral blood mononuclear cell (PBMC) samples may be thawed and washed in deficient RPMI media supplemented with 4% FCS. Biotin-coupled antigen (DBY-2 or DBX-2) may be added to the cells and 20 minutes later, a "cocktail" of fluorochrome conjugated monoclonal antibodies detecting CD19, CD2F, CD43, CD5, CD23, IgM and IgG, CD27 and dead cells may be added. Following 20 minute incubation, cells may be spun and washed and incubated for 20 min with fluorochrome-conjugated streptavidin. Data may be collected for $1-5\times10^6$ cells on a LSRII flow cytometer (BDBiosciences.com). The data may be analyzed using FlowJo (TreeStar.com) and further analyzed with Excel and Prism (GraphPad software, Inc).

Most parameters measurable by flow cytometry can also be measured by other techniques well-known in the art. These techniques include, but are not limited to, analytical cytology (e.g., microfluorimetry), standard microscopic-based cytometric analysis, physical sorting (e.g., panning), standard immunohistochemical techniques and the like.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The applicability of the described invention was demonstrated by the quantification of CD8α antigen concentration on human T-cells in stable binding conditions as compared with those obtained with the Quanti-BRITE calibration system.

Materials and Methods

Monoclonal Antibodies

FITC-labeled anti-CD3 IgG mouse monoclonal antibody (BD Pharmingen, Cat #555332, Lot #30100) was used in experiments with human blood cells.

PE-labeled RPA-T8 (anti-CD8α) IgG mouse monoclonal antibody (BioLegend, Cat #301008, Lot # B 137490) was used for all kinetic experiments. The manufacturer claims the concentration of $1.9\times10^{13}$ 1/mL ($3\times10^{-8}$ M). This lot was prepared to consist almost exclusively of 1:1 PE-to-antibody conjugates.

Calibration Beads

Quanti-BRITE PE Beads (Becton Dickinson, Cat #340495, Lot #30746, Lot #77602) were used in accordance with manufacturer's protocol to relate the measured signal to the number of PE-antibody molecules. Briefly, the Quanti-BRITE PE tube was removed from the foil pouch just prior to use and reconstituted using 0.5 mL of buffer, such as PBS with azide plus 0.5% BSA, and vortexed. CELLQuest™ was launched on the flow cytometry instrument. Using the setup mode, all parameters for the cellular assay were adjusted. Next, the flow cytometry instrument was properly compensated, for example, with CaliBRITE™ beads. The Quantitation Acquisition document located in the Sample Files folder in the CELLQuest folder (only in CELLQuest 3.1 and later versions) was opened. The document was modified to include plots for the cellular assay. Next, the QuantiBRITE PE tube was run, thresholding on FSC or SSC, and 10,000 events were collected. The FSC and SSC parameter settings can be changed to gate on bead singlets without altering quantitation. All instrument settings for fluorescence and compensation must be the same as the cellular assay settings. The gate was adjusted around the bead singlets on the FSC-H vs SSC-H plot. The singlet bead population was analyzed using a histogram plot of FL2-H in linear values. Markers were adjusted around the four bead peaks. The histogram statistics were viewed, making sure that the geometric means were displayed. Next, the Histogram Statistics view was selected and Quantitative Calibration was chosen from the Acquire menu. The Copy Means button was clicked in order to copy the geometric means of the four bead peaks from the histogram statistics window. The lot-specific PE/bead values provided on the flyer packaged in the QuantiBRITE PE kit were entered. Next, the tab key was pressed; then Calibrate was clicked for CELLQuest to perform the regression analysis, and to display the slope, intercept, and correlation coefficient. After calibration, the Experiment document was saved. The same instrument settings and Experiment document was used to acquire cellular assay samples. All subsequently collected data files will save the information displayed in the Quantitative Calibration window. An active Quantitative Calibration window can be printed by selecting Print from the File menu. QuantiCALC™ can read the regression information for analysis of assay files. The signal per PE-antibody molecule was determined in each experiment.

Microbeads

Antibody capture (compensation) beads coupled with anti-Mouse Ig kappa (Becton Dickinson, Cat #552843, Lot #2230632) were used in the kinetic experiments as described below.

Human Blood Sample Preparation 18 ml of peripheral blood was drawn from a healthy volunteer with informed consent by venipuncture and placed into a polystyrene tube containing the potassium salt of ethylene diamine tetraacetic acid (EDTA). The blood was transferred into a 50 ml conical tube, rinsed with 1×PBS and refilled to 50 ml with 1×PBS. 25 ml of the mixture was placed on 15 ml Ficoll (2 tubes) (Lymphoprep, Cat #07801) and centrifuged 20 min at 700 g, 20° C. The upper phase was aspirated and the zone containing PBMCs (Peripheral blood mononuclear cells) was transferred into a new 50 ml tube with 10 ml 1×PBS (2× Ficoll into one 50 ml tube), filled to 50 ml with 1×PBS (with 10% FCS) and centrifuged 10 min at 450 g, 20° C. The supernatant was discarded and the pellet resuspended in 1 ml 1×PBS, filled to 50 ml and centrifuged 10 min at 200 g, 20° C. The supernatant was discarded and the pellet resuspended in 100 μL of PBS and 10 ul of FITC-labeled CD3 antibody and incubated on ice for 20 minutes in the dark. After incubation, the cells were washed in PBS (with 10% FCS) and pelleted by centrifugation for 10 min at 450 g, 20° C. The supernatant was discarded and the pellet resuspended in 1 ml of Phosflow™ Lyse/Fix Buffer (Becton Dickinson, Cat#558049) and 3 ml of PBS (with 10% FCS) and incubated at 20° C. for 20 minutes. After incubation, the cells were washed in PBS (with 10% FCS) and pelleted by centrifugation for 10 min at 450 g, 20° C. Excess supernatant was aspirated and discarded. The cells were resuspended in 450 μl of PBS (with 10% FCS) prior to use in the kinetic experiment described below.

Kinetic Experiment Overview

Time series of mean fluorescence intensity (MFI) (hereinafter referred to as kinetics) were measured as follows. A volume $v_2$ of anti-Mouse Ig kappa bead suspension or human blood cell suspension was resuspended in buffer (50 and 40 μl of PBS, respectively). Then, volume $v_1$ of PE-labeled antibody was added to the mixture of microbeads or cells to initiate the antigen-antibody binding reaction. At time points 0.16 min, 1 min, 3 min, 9 min, 27 min and 81 min, 8 μl of the mixture were resuspended in PBS (300 μL) in order to stop the reaction. After all sampling was completed, the microbeads or cells were analyzed with a flow cytometer. The reactions and measurements were carried out at room temperature.

The reaction kinetics of the microbeads and of the cells was measured for five different combinations of microbead-antibody concentrations and nine combinations of cell-antibody concentrations (i.e., 5 or 9 $v_1$, $v_2$ combinations). The antibody concentrations varied from $1.5 \times 10^{-10}$ M to $1 \times 10^{-8}$ M.

Instrument and Data Acquisition 3000 microbeads and 30,000 cells were collected at each time point for the human blood sample, using an LSRII digital flow cytometer (BD Biosciences) with 5 lasers (355, 405, 488, 561, and 640 nm), 2 light scatter detectors, and 14 fluorescent detectors utilizing DiVa software (BD Biosciences). MFIs in the PE fluorescence channel for microbeads were calculated in each measured sample for single microbeads as gated in a forward light scattering (FSC) versus side light scattering (SSC) cytogram. MFIs in the PE fluorescence channel for the $CD3^+CD8^+$ subset of cells were obtained by gating the lymphocytes singlets in the light scattering (FSC, SSC) cytograms and the $CD3^+CD8^+$ lymphocyte subset in CD3 versus CD8 cytograms. The LSR-II electronics includes both analog and digital baseline restoration that prevents free dye in the samples from affecting the MFIs of the microbeads or cell populations. In order to evaluate the concentrations of beads and cells in samples we performed volumetric measurements using the sample flow rate described in the datasheet for the LSRII digital flow cytometer (a higher flow rate, e.g., 35-60 μL/min, is generally used for qualitative measurements; a lower flow rate, e.g., around 12 μL/min, is generally used in applications where greater resolution and quantitative measurements are critical). All the measurements were made at a medium speed of about 100 particles per second. The stability of flow rate was confirmed by the linearity of number of events versus time ($R^2=0.9988$).

In our experiments, the diffusion-limited condition assumed in the reaction model only becomes applicable after the initial mixing of microbeads or cells with antibody. A substantial amount of antibody binding occurs during this initial mixing, leading to relatively large MFIs at the earliest time points. This accelerated reaction before the first time point can be accommodated in the model by adding a time shift parameter $t_0$ for the difference between the apparent and the actual starting times. The fitted values for $t_0$ will also adjust for small effects like cell autofluorescence and possible incomplete stopping of the reaction after the final dilution.

Acceleration of the Reaction During Mixing

To test the hypothesis of reaction acceleration during mixing, a time-series of MFIs were measured with the same concentrations of reagents, with and without additional mixing (FIG. 1). The addition of a 5 second vortexing after minimal initial mixing resulted in an effective time shift $t_0$ of about 4 minutes.

Figure 2:
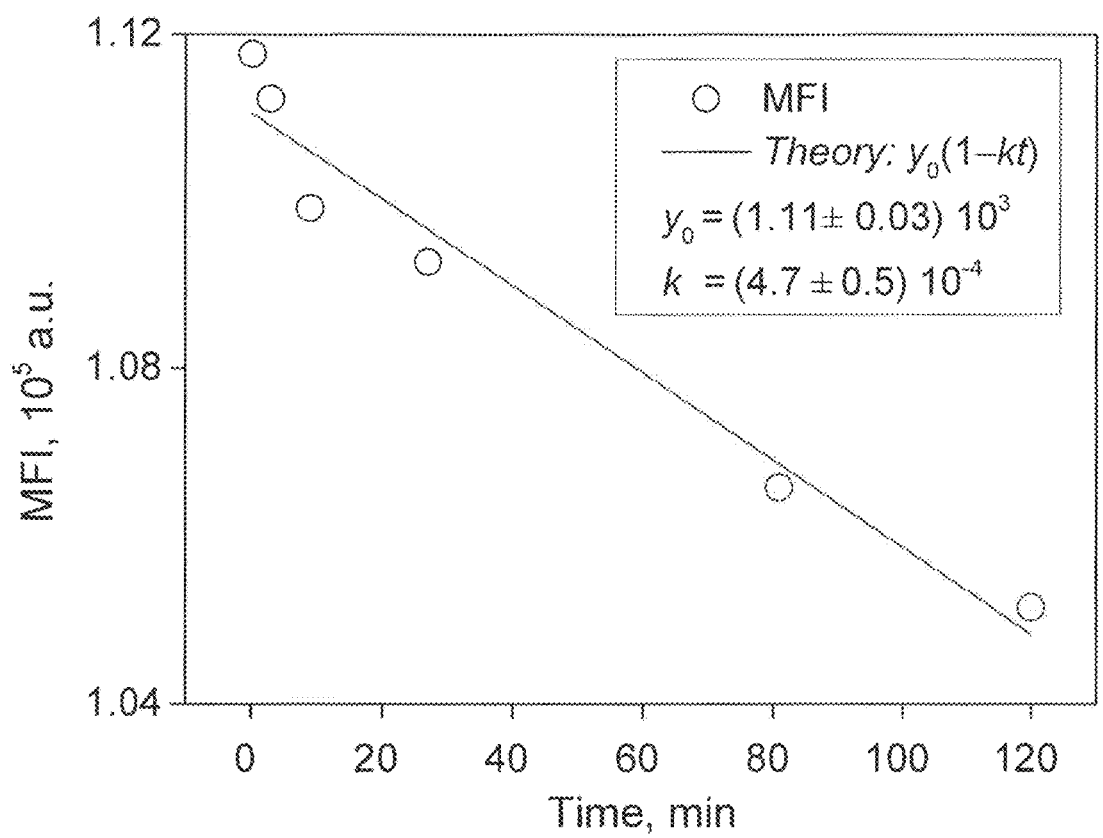
FIG. 2 depicts a decrease in mean fluorescence intensity (MFI) after 25-fold dilution of the reaction mixture after the incubation of $10^{-9}$ M of receptors (tethered to beads) with $10^{-8}$ M of antibody during 81 min. Linear fitting was used to evaluate the rate constant of the decrease k, which is an estimate of reverse reaction rate constant $k_-$.

After final dilution by a certain dilution factor, the reaction rate slows down by that same certain dilution factor. In the case of a long delay between dilution and measurements, continuing slow reaction can contribute to time shift effect. However, this effect can be minimized by optimization of the dilution and measurement procedures. Ideally, the MFI should be measured just after dilution, but this can be impractical, especially when using flow cytometer in a shared research laboratory. Instead, the dilutions for all of the time points were performed and all of the samples were measured in a short time at the end. In this case, the recommendation is to minimize the gap between the end of the kinetics sequence and the start of measurements. In our experiments, this gap was about one hour, which changes the MFI value by no more than 4% (FIG. 2). Without being bound by theory, the stopping procedure might be improved by including an excess of unconjugated antibody in the dilution medium.

General Equation for the Temporal Evolution of Mean Fluorescence Intensity (MFI)

To describe the temporal evolution of the fluorescence profile, the mathematical model for reversible antibody-antigen binding was used (Orlova D et al. Distribution function approach to study the kinetics of IgM antibodies binding to FcγRIIIb (CD16b) receptors on neutrophils by Flow Cytometry. Journal of Theoretical Biology. 2011. Vol. 290:1-6. doi:10.1016/j.jtbi.2011.08.026). The model is applicable for independent binding sites, i.e., when the size of the binding site is much less than the distance between binding sites (Nekrasov V M et al. Brownian aggregation rate of colloid particles with several active sites. The Journal of Chemical Physics. 2014. Vol. 141(6):064309. doi: 10.1063/1.4892163). The model was extended by accounting for time shift $t_0$. This model allows the temporal evolution of mean fluorescence intensity (MFI) ($\bar{y}$) to be analyzed with respect to the following parameters: fluorescence signal per antibody molecule $\alpha$, concentration of particles (beads or cells, for instance) c, total concentration of binding sites $X_0$, total concentration of antibody $A_0$, reaction rate constant $k_+$ and the equilibrium constant K:

$$\bar{y} = \alpha \frac{A_0}{c} \frac{y'_1 y'_2 \cdot [\exp(k_+ A_0 (y'_1 - y'_2)(t + t_0)) - 1]}{y'_1 \cdot [\exp(k_+ A_0 (y'_1 - y'_2)(t + t_0)) - 1] - y'_2}, \quad (1)$$

$$y'_{1,2} = \frac{1}{2}\left(1 + \frac{X_0}{A_0} + \frac{K}{A_0}\right) \pm \frac{1}{2}\sqrt{\left(1 + \frac{X_0}{A_0} + \frac{K}{A_0}\right)^2 - 4\frac{X_0}{A_0}}$$

Although some experiments included kinetics series in non-saturating conditions, the reverse reaction has small influence on the kinetics. This was confirmed by the following observations: after dilution of beads incubated with the excess of antibody (~$10^{-9}$ M of antibody to ~$10^{-10}$ M of receptors) for 81 min, the MFI decreases in time with the initial relative rate near $5 \times 10^{-4}$ min$^{-1}$ (FIG. 2). Since the decrease is due to the reverse reaction, this value is an estimate for the reverse reaction rate constant. Together with the measured reaction rate constant, this gives the equilibrium constant K in order of $10^{-12}$ M. Equation (1) was numerically tested for this value of K. The results indicated that the reverse reaction makes a negligible contribution, changing the saturation value by less than 0.5% (data not shown).

Irreversible Binding: Relationship Between Parameters

Hereinafter we neglect the reverse reaction, i.e., consider the dissociation constant to be zero (K→0). In this case, Eq. (1) can be reduced as follows. First, we rewrite all the parameters with respect to the concentration of particles c:n=$X_0$/c—mean number of binding sites per particle (the parameter of interest, which is to be determined), $a_0 = A_0/c$, $\check{k}_+ = k_+ c$. This leads to the following simplified equation (1):

$$\bar{y} = \alpha n \frac{\exp\left(\check{k}_+ a_0 \left(1 - \frac{n}{a_0}\right)(t + t_0)\right) - 1}{\exp\left(\check{k}_+ a_0 \left(1 - \frac{n}{a_0}\right)(t + t_0)\right) - n/a_0} = \quad (2)$$

$$P_1 \frac{\exp[P_2(1 - P_3)(t + P_4)] - 1}{\exp[P_2(1 - P_3)(t + P_4)] - P_3},$$

where $P_1 = \alpha n$, $P_2 = \check{k}_+ a_0$, $P_3 = n/a_0$ and $P_4 = t_0$. The equation (2) is a function of 4 parameters, and they can be determined by fitting experimental kinetics data. The MFI evolution itself is in general controlled by $t_0$ and 4 parameters of interest ($\alpha$, n, $k_+$ and $a_0$). Therefore, we need to know at least one of the 4 parameters independently in order to determine the other parameters.

Consider that we want to determine the number of binding sites per cell n (antigen quantification) given the measured kinetics. Let all the parameters $P_1$-$P_4$ be determined by fitting. Three situations would allow us to complete the evaluation:

1. The Fluorescence Signal Generated Per Antibody Molecule $\alpha$ is Known from Calibration (i.e., Use of a Calibrator).

This situation is the most typical. In this case, the number of binding sites n can be found as $P_1/\alpha$. Moreover, n can be estimated from just the last kinetic point, assuming that saturation is achieved at that time.

2. The Antibody Concentration $A_0$ is Known/Previously Measured.

In this case, n=$P_3 a_0$=$P_3 A_0$/c. The antibody concentration is usually provided in the datasheet, however, the accuracy of this value is rarely given. It should be double-checked by other methods prior to use for antigen quantification. Furthermore, the concentration may be subject to variation over time due to antibody aggregation.

3. The Rate Constant $k_+$ for the Given Binding Reaction is Known/Previously Measured.

In this case, n=$P_3 P_2/\check{k}_+$=$P_3 P_2/k_+ c$. Reaction rate constants are known for relatively few antigen-antibody pairs. However, once the rate constant is known, it allows one to measure n independently of instrument settings, reagent concentrations and time. In this sense, $k_+$ is the most universal parameter. However, n is determined by the combination of two model parameters (instead of one), which could result in slightly larger uncertainty compared to previous cases.

It should be noted that fitting by equation (2) allows one to quantitate the antigen on target particles as soon as one other parameter of the system is known. This could be the signal per antibody molecule $\alpha$, the antibody concentration $a_0$ or reaction rate constant $\check{k}_+$. In this sense, the time-consuming repetitive calibration procedure is equivalent to knowing the rate constant, which is the universal characteristic of the interacting molecules. Application of the rate constant approach may be limited by the lack of measured $k_+$ values for most antigen-antibody pairs of interest. Therefore, preliminary experiments to evaluate $k_+$ are likely to be necessary. For example, vendors could measure the value of $k_+$ in-house using an $\alpha$ value calibration once for each specific lot of antibody and provide this information in their product description. Another limitation may be the dependence of the reaction rate constant on temperature, pH and other parameters. These parameters, however, can be controlled during the measurement.

Determination of model parameters by fitting constitutes a solution to the nonlinear regression problem, which gives values of $P_1$-$P_4$ together with their precision. The latter depends on the experimental conditions. For example, in antibody excess, equation (2) tends to $\bar{y}=\alpha n$ (i.e., independent of $a_0$ and $\check{k}_+$), which results in large errors in determining these parameters. Without being bound by theory, a similar situation may occur in the case of receptor excess.

Equation (2) was used to fit the experimental kinetics of MFI. In each experiment the time shift $t_0$ was determined separately for each kinetics time series, and other parameters ($P_1$-$P_3$) were the same with adjustments for different dilutions. Fitting was made with OriginLab Origin 9.1 using Levenberg-Marquardt algorithm. A multistart procedure was employed in which the fitting was performed many times at different initial values of the parameters. One solution was observed that agreed visually with the experiment and had a squared error norm that was less than the other solutions. This procedure also resulted in parameters consistent with preliminary estimates.

Example 1. Anti-Kappa Beads: Multi-Kinetics Fitting

In this study, time series of mean fluorescence intensity (MFI) (i.e., kinetics) were measured using anti-Mouse Ig-kappa capture beads.

Kinetic experiments were performed with anti-Mouse Ig-kappa capture beads. The fluorescently-labeled monoclonal antibody (anti-CD8α-PE) was added to the bead suspension to initiate antibody-antigen binding. The mean fluorescence intensity (MFI) of approximately 3000 beads was measured for each time point (0.16, 1, 3, 9, 27 and 81 min).

Figure 3:
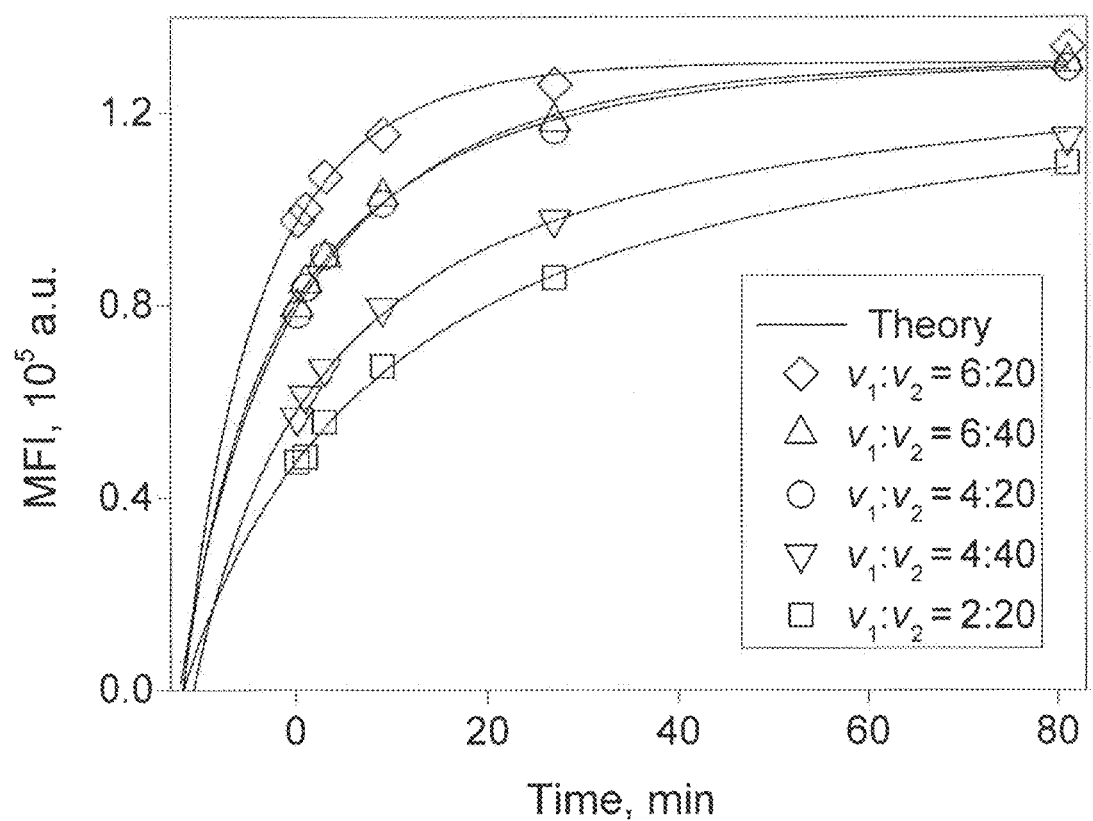
FIG. 3 depicts a measured time-series of mean fluorescence intensity (MFI) (symbols) and theoretical curves (solid lines) obtained by fitting. Volumes $v_1$ and $v_2$ of antibody and beads, respectively, were added to a constant volume of the reaction suspension
Figure 4:
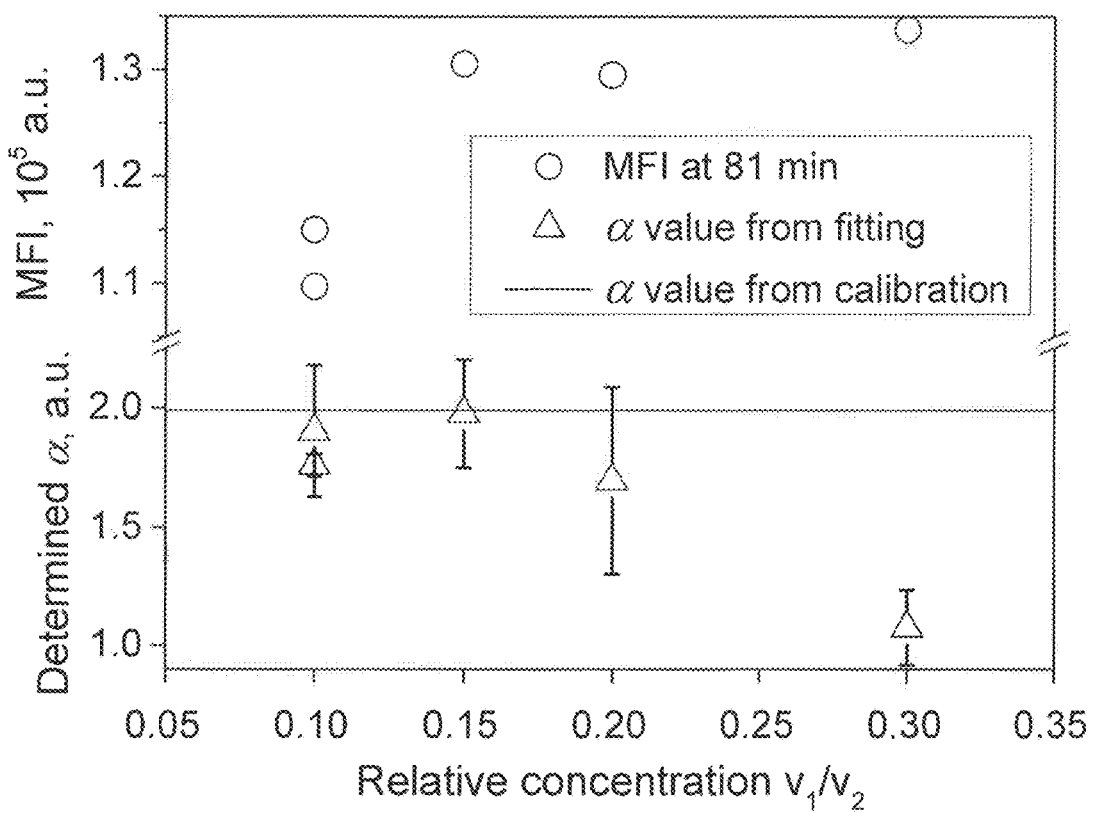
FIG. 4 depicts a titration curve (circles) and signal per antibody molecule estimates $\alpha$ (triangles) with their precision (error bars). Volumes $v_1$ and $v_2$ of antibody and beads, respectively, were added to a constant volume of buffer. The $\alpha$ value closest to the real value is achieved at the transition point (when $n \approx a_0$).

Five (5) time-series of the MFI (kinetics) were measured for different ratios of antibody:antigen by mixing different volumes of reagents (2 to 6 μL of antibody and 20 to 40 of beads) in order to span a range of saturating and non-saturating conditions. Five (5) measured kinetics series are shown in FIG. 3. Composite fitting of these data was performed with the theoretical expression for the evolution of mean fluorescence over time in Equation (2) with appropriate adjustments for v1 and v2 of each time series. The corresponding curves are shown as solid lines in FIG. 3.

Fitted parameters corresponding to v1:v2=1:1 are presented in Table 1. Precision for these parameters was calculated to be 0.7% for $\alpha \cdot n$, 6% for $\check{k}_+ \cdot a_0$ and 4% for $n/a_0$ (data not shown). $P_3 = n/a_0 = 9.5 \times 10^{-2}$ adjusted for the actual values of v1:v2=4:40 and 2:20 gave an antibody/binding site ratio ($a_0/n$) of 1.05 which does not label to saturation in 81 minutes (FIG. 3). The highest curve, with v1:v2=6:20 has $a_0/n=3.15$, is very close to saturation at 27 minutes (FIG. 3). The values of initial time $t_0$, are essentially the same for all kinetics (~12 min), indicating reproducibility in the mixing procedure.

TABLE 1

Parameters of fitting and their standard errors.

| Parameter | Value | Standard Error |
|---|---|---|
| $P_1 = \alpha \cdot n$ | $1.30 \times 10^5$ | $1 \times 10^3$ |
| $P_2 = \check{k}_+ \cdot a_0$, min$^{-1}$ | 1.7 | 0.1 |
| $P_3 = n/a_0$ | $9.5 \times 10^{-2}$ | $4 \times 10^{-3}$ |
| $t_{01}$, min | 12 | 1 |
| $t_{02}$, min | 12 | 1 |
| $t_{03}$, min | 12 | 1 |
| $t_{04}$, min | 11 | 1 |
| $t_{05}$, min | 12 | 1 |

Example 2. Use of Reaction Rate Constant to Determine Antigen Quantity and Physical Parameters α, $a_0$, k+ and n The parameters shown in Table 1 can be evaluated by fitting without calibration. However, these parameters are not enough for antigen quantitation. Thus, Quanti-BRITE beads were used to obtain the signal per antibody molecule α=1.99±0.01. Using the fitted value of $P_1=\alpha \cdot n=(1.30+0.01) \times 10^5$, the amount of antigen per bead $n=65.6 \times 10^3$ was obtained. Next, $a_0=69 \times 10^4$ and $\check{k}_+=2.5 \times 10^{-6}$ min$^{-1}$ were calculated.

Given the value of α and assuming that the maximal fluorescence intensity observed in FIG. 3 represents full labeling, n (number of binding sites/amount of antigen) was determined without any fitting and the result obtained was similar to the result obtained using Quanti-BRITE beads ($n=67.2 \times 10^3$ without fitting; $n=65.6 \times 10^3$ with Quanti-BRITE beads). The standard (Quanti-BRITE beads) approach to antigen quantitation confirmed the fitting results, but it does not provide the other parameters of interest (α, $a_0$, $k_+$).

Since the relationship between fitting parameters P1-P3 and physical parameters α, $a_0$, $\check{k}_+$ and n is unambiguous, α, $a_0$ or $\check{k}_+$ can be used equivalently to find n, thus avoiding the use of direct calibration. For example, if the signal per antibody molecule α is not measured, but another parameter is known and has a value shown in Table 2, the values of other parameters would be unchanged but expressed by different combinations of $P_i$. By way of example, if a is known, $n=P_1/\alpha$; if $\check{k}_+$ is known, $n=P_3 \cdot P_2/\check{k}_+$. However, the precision would be different in these cases, since each $P_i$ has its own uncertainty, as well as the uncertainty in the known parameter. In the case of small uncertainties, the overall precision can be approximated by adding the relative errors. The corresponding standard errors (assuming that the known parameter is absolutely accurate) are shown in Table 2 for all three situations discussed (1. The fluorescence signal generated per antibody molecule α is known from calibration; 2. The antibody concentration $A_0$ is known/previously measured; 3. The rate constant $k_+$ for the given binding reaction is known/previously measured). The largest relative errors were calculated to be about 10%.

TABLE 2

Values of parameters determined from fitting and calibration. Precision of parameters for three different situations are also shown.

| Parameter | Value | SE (α is known) | SE ($a_0$ is known) | SE ($\check{k}_+$ is known) |
|---|---|---|---|---|
| A | 1.99 | — | 0.1 | 0.2 |
| $a_0$ | $69 \times 10^4$ | $3 \times 10^4$ | — | $4 \times 10^4$ |
| $\check{k}_+$, min$^{-1}$ | $2.5 \times 10^{-6}$ | $0.3 \times 10^{-6}$ | $0.1 \times 10^{-6}$ | — |
| N | $65.6 \times 10^3$ | $0.4 \times 10^3$ | $2.8 \times 10^3$ | $6.6 \times 10^3$ |

SE = Standard Error

Using reaction rate constant $\check{k}_+$ instead of the signal per antibody molecule α as the known parameter for evaluating other parameters is advantageous. First, the rate constant is independent of the specific instrument and can be recalculated for different fluorochrome labels (using the theory published in Nekrasov V M et al. Brownian aggregation rate of colloid particles with several active sites. The Journal of Chemical Physics. 2014. Vol. 141(6):064309. doi: 10.1063/1.4892163). No experiment-specific calibration would be needed. Second, the rate constant is determined only by the interacting antibody-antigen pair (assuming that the temperature and pH are controlled). Therefore, it would be valuable to develop a database with rate constants for different couples of specific molecules. However, the concentration of cells must be known in order to relate $k_+$ and $\check{k}_+$. The concentration of cells, for example, can be estimated without any additional measurements using a cytometer with volumetric sample delivery or by volumetric measurements using a LSRII digital flow cytometer. The concentration of beads amounted to $6.4 \times 10^6$ ml$^{-1}$; the corresponding absolute values $k_+$ ($[2.3 \pm 0.3] \times 10^8$ M$^{-1}$ min$^{-1}$) and $A_0$ ($[4.4 \pm 0.2] \times 10^{12}$ mL$^{-1}$) are shown in Table 4.

Example 3. Use of One-Kinetics or Two-Kinetics to Determine a and n without Calibration From a practical point of view, it is undesirable to measure several kinetics because it is time-consuming. Conversely, one curve generally is not sufficiently informative to give four parameters with small errors. In this study, one time series or two time series was used to determine whether the physical parameters a and n could be obtained without calibration.

The rate constant and the antibody concentration (or either the rate constant or the antibody concentration and their product $P_2$) were considered known (i.e., determined from preliminary experiments). For this example, the rate constant and $P_2$ values from multi-kinetics fitting (Table 1) were used. These values were fixed and fitting for each of the measured kinetics were performed.

The closest match to the calibrated α value and the lowest standard error were found for $v_1/v_2=0.15$ where the antibody/binding site ratio was about 1.6. The fits for $v_1/v_2=0.10$ and 0.20 had higher standard errors, and the highest concentration fit missed the calibrated value entirely. Based on this data, single kinetics fitting was useful only if the antibody/binding site ratio was close to the optimum.

Figure 5:
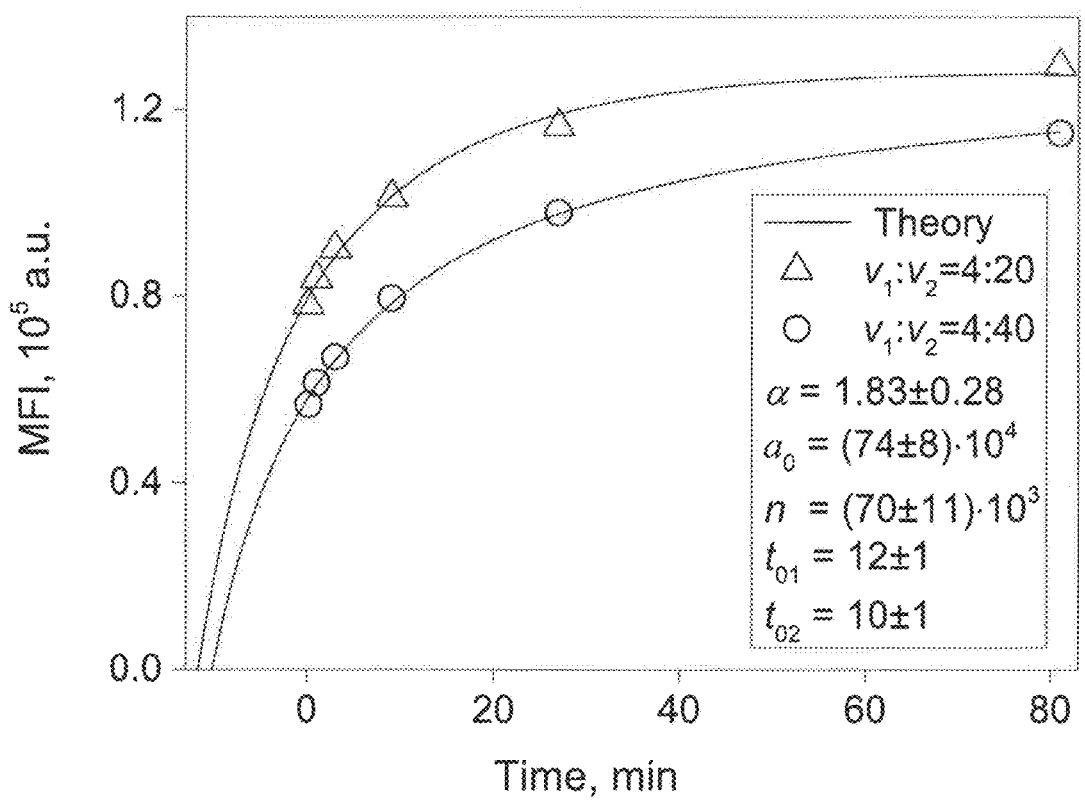
FIG. 5 depicts an example of double-kinetics fitting. The rate constant has been fixed (taken to be known a priori).

Another possibility is to use two-kinetics on opposite sides of the optimal ratio. Two curves can be used to evaluate all parameters simultaneously, without fixing $P_2$. FIG. 5 shows the example of two-kinetics (or double-kinetics) fitting. Although the value of 1.83±0.28 was within one standard error of the calibrated value, it was not as good as the standard error estimated for the full composite fit of 0.2 (See, Table 2).

Example 4. Use of Human T-Cells to Determine Physical Parameters With and Without Calibration Human cytotoxic T-cells interact with antigen-presenting cells through T-cell receptors (TCR) that bind major histocompatibility complex-1 (MHC-I) tetramer. The CD8 co-receptor plays a critical role for this binding (Campanelli R et al. Human CD8 co-receptor is strictly involved in MHC-peptide tetramer-TCR binding and T cell activation. International Immunology. 2002. Vol. 14:39-44. doi: 10.1093/intimm/14.1.39). CD8 increases the binding rate by two orders of magnitude, approximately up to the CD8-MHC I reaction rate constant. The latter is in the order of $10^5$ M$^{-1}$ s$^{-1}$ (Gakamsky D M et al. CD8 kinetically promotes ligand binding to the T-cell antigen receptor. Biophysical Journal. 2005. Vol. 89:2121-33. doi: 10.1529/biophysj.105.061671). The cooperative effect is also confirmed by the fact that anti-CD8 antibody blocks TCR-MHC I binding (Denkberg G et al. Critical role for CD8 in binding of MHC tetramers to TCR: CD8 antibodies block specific binding of human tumor-specific MHC-peptide tetramers to TCR. The Journal of Immunology. 2001. Vol. 167:270-276. doi: 10.4049/jimmunol.167.1.270). This suggests that the CD8-anti-CD8 reaction rate is much faster. However, this reaction has not been well-characterized. That is, the rate constant is not available in the literature. By contrast, the number of CD8 co-receptors on the T-cell surface n has been measured by flow cytometry and amounted to ~2.5×10$^4$ (Jun Huang. A Kinetic Study of the T Cell Recognition Mechanism. PhD thesis, Georgia institute of technology. 2008).

Figure 6:
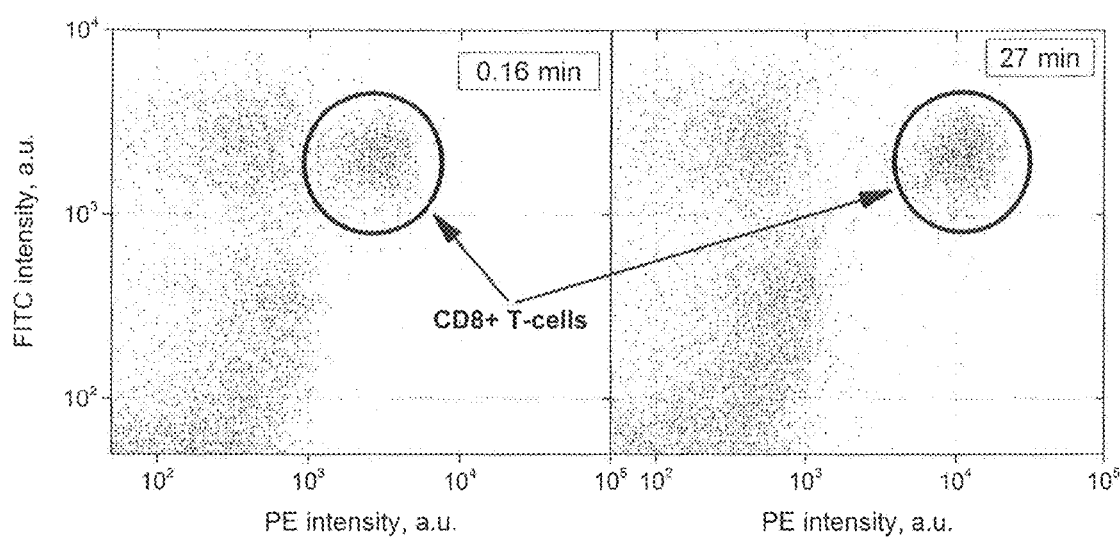
FIG. 6 depicts growth of mean PE intensity of a population of human cytotoxic T-cells over time: (left) 0.16 min and (right) 27 min after addition of IgG phycoerythrin (PE)-labeled antibodies specific to CD8α. Each plot includes cells in the lymphocyte peak as gated on a plot of forward light scattering (FSC) versus side light scattering (SSC). The axes: Y is the fluorescence intensity in the fluorescein isothiocyanate (FITC) channel (FITC-labeled CD3 antibody); X is the fluorescence intensity in the PE channel (PE labeled CD8α antibody). Each dot corresponds to one cell.
Figure 7:
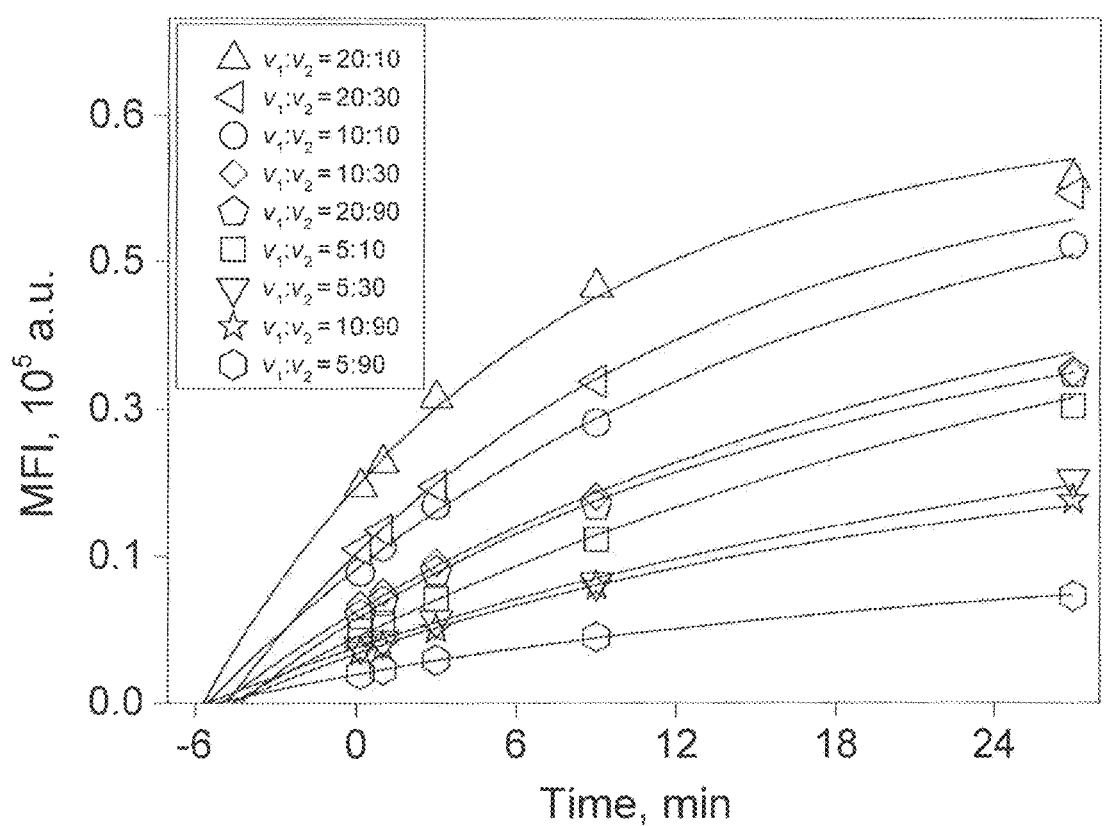
FIG. 7 depicts a kinetic experiment for T-cells (symbols) and theoretical curves (solid lines) obtained by fitting. Volumes v1 and v2 of antibody and cells, respectively, were added to a constant volume of the reaction buffer.

Kinetics experiments for CD8-antiCD8α binding were carried out as described. Briefly, a volume $v_2$ of human blood cell suspension was resuspended in buffer (40 μl of PBS). Then, volume $v_1$ of PE-labeled antiCD8α antibody was added to the mixture of cells to initiate the antigen-antibody binding reaction. Then, at certain time points (0.16 min, 1 min, 3 min, 9 min, 27 min and 81 min) 8 μl of the mixture were resuspended in PBS (300 μL) in order to stop the reaction. After all sampling was completed, the cells were analyzed with the flow cytometer. The reactions and measurements were carried out at room temperature. The evolution of the CD8+ T-cell fluorescence intensity is shown in FIG. 6. The similarity of the CD3+CD8-populations at about 400 MFI in both the 0.16 min and 27 min panels indicates that non-specific binding is negligible in this system. Kinetics were measured for 9 combinations of antibody and cell concentration (FIG. 7) and limited the time series to 27 min instead of 81 min for ease of measurement. Each of the kinetics consisted of 5 time points: 0.16, 1, 3, 9 and 27 min. A 10-fold pre-dilution of the antibody was made to provide antibody in the range of maximum sensitivity in convenient volumes.

The fitting results are shown in Table 3. The signal per antibody molecule α=2.10±0.02 obtained from Quanti-BRITE calibration and the cell concentration obtained using an LSRII digital flow cytometer (See, Instrument and Data Acquistion) was used to measure the mean number of receptors per cell n, the antibody concentration $A_0$ and rate constant $k_+$. All values obtained are shown in Table 4 (right column) together with values obtained in experiments with microbeads (left column).

TABLE 3

Parameters of fitting and their precision.

| Parameter | Value | Standard Error |
|---|---|---|
| α · n | 61 × 10$^3$ | 1 × 10$^3$ |
| $\check{k}_+ \cdot a_0$, min$^{-1}$ | 0.29 | 0.02 |
| n:$a_0$ | 2 × 10$^{-2}$ | 2 × 10$^{-3}$ |
| $t_{01}$, min | 5 | 1 |
| $t_{02}$, min | 5 | 1 |
| $t_{03}$, min | 6 | 1 |
| $t_{04}$, min | 5 | 1 |
| $t_{05}$, min | 5 | 1 |
| $t_{06}$, min | 5 | 1 |
| $t_{07}$, min | 5 | 1 |
| $t_{08}$, min | 5 | 1 |
| $t_{09}$, min | 4 | 1 |

The determined $A_0$ is similar to, but slightly larger than, the value obtained in the microbead experiment. However, both determined $A_0$ values are approximately 5 times lower than specified in the reagent documentation (1.9×10$^{13}$ 1/mL (3×10$^{-8}$M)). Without being limited by theory, this may be attributed to, for example, degradation of antibody over time or aggregation and sedimentation of molecules in the bottle.

TABLE 4

Absolute values for microbeads and T-cells.
Estimated values and their standard errors are given in parentheses.

| Parameter | Microbeads (anti-mouse κ) | T-cells (CD8) |
|---|---|---|
| N | $(65.6 \pm 0.4) \times 10^3$ | $(28.8 \pm 0.6) \times 10^3$ |
| $c_0$, mL$^{-1}$ | $6.4 \times 10^6$ | $4.0 \times 10^6$ |
| $A_0$, mL$^{-1}$ | $(4.4 \pm 0.2) \times 10^{12}$ | $(5.6 \pm 0.5) \times 10^{12}$ |
| $k_+$, M$^{-1}$min$^{-1}$ | $(2.3 \pm 0.3) \times 10^8$ | $(3.1 \pm 0.4) \times 10^8$ |

The rate constant $k_+$ was determined to be about one third higher than that of the Ab-beads reaction. Without being bound by theory, this difference may be related to the different binding sites of the antibody, since the reaction rate is approximately proportional to the third power of the size of the binding site (Orlova D et al. Distribution function approach to study the kinetics of IgM antibodies binding to FcγRIIIb (CD16b) receptors on neutrophils by Flow Cytometry. Journal of Theoretical Biology. 2011. Vol. 290:1-6. doi:10.1016/j.jtbi.2011.08.026). Considering the variability among human subjects, the number of receptors per cell is in agreement with the literature (Jun Huang. A Kinetic Study of the T Cell Recognition Mechanism. PhD thesis, Georgia institute of technology. 2008).

As described, the binding rate constant $k_+$ can be used instead of calibration. Parameter values and their standard errors for the three different situations described (1. The fluorescence signal generated per antibody molecule α is known from calibration; 2. The antibody concentration $A_0$ is known/previously measured; 3. The rate constant $k_+$ for the given binding reaction is known/previously measured) are presented in Table 5. This data shows that knowledge of the reaction rate constant can replace the repetitive calibration procedure.

TABLE 5

Values of parameters determined from fitting and calibration. Precision of parameters for three different situations are also shown.

| Parameter | Value | SE (α is known) | SE ($a_0$ is known) | SE ($\check{k}_+$ is known) |
|---|---|---|---|---|
| A | 2.10 | — | 0.2 | 0.4 |
| $a_0$ | $141 \times 10^4$ | $13 \times 10^4$ | — | $10 \times 10^4$ |
| $\check{k}_+$, min$^{-1}$ | $2 \times 10^{-6}$ | $0.3 \times 10^{-6}$ | $0.1 \times 10^{-6}$ | — |
| N | $28.8 \times 10^3$ | $0.6 \times 10^3$ | $3 \times 10^3$ | $5 \times 10^3$ |

SE = Standard Error

Using the binding rate constant $k_+$, it was possible to estimate the radius b of the binding site (a circular approximation of the shape of the site placed on a spherical reagent) by employing the following expression (Nekrasov V M et al. Brownian aggregation rate of colloid particles with several active sites. The Journal of Chemical Physics. 2014. Vol. 141(6):064309. doi: 10.1063/1.4892163):

$$k_+ = N_1 N_2 \frac{k_B T b^3}{12\eta} \left( \frac{1}{R_1} + \frac{1}{R_2} \right)^3 \quad (3)$$

where η is the viscosity of the media, $k_B$ is the Boltzmann constant, T is the temperature; $R_1$ and $R_2$ are radii, $N_1$ and $N_2$ are valences of the first and second reactants, correspondingly. The radius of the beads was calculated to be 3 μm (approximately the same as the radius of the cells). The radius of antibody molecules can be estimated from the diffusion coefficient using Stokes-Einstein equation (Nekrasov V M et al. Brownian aggregation rate of colloid particles with several active sites. The Journal of Chemical Physics. 2014. Vol. 141(6):064309. doi: 10.1063/1.4892163):

$$D = \frac{k_B T}{6\pi\eta R} \quad (4)$$

The diffusion coefficient of the molecule can be estimated using the known relationship between the diffusion coefficient D (in cm$^2$ s$^{-1}$) and the molar mass M (in Da) of a protein (in water at room temperature) (Ibrahim, M., Gongwei, Z., Junjie, Z., 1998. Determination of diffusion coefficients proteins by flow injection analysis and its application to estimation molecular masses of proteins. Instr. Sci. Technol. 26 (4), 333-341):

$$\text{Log } M = -16.88 - 3.51 \text{ Log } D \quad (5)$$

It is known that the anti-CD8α molecule is a 150 kDa type IgG immunoglobulin with the valence N=2. Phycoerythrin (PE) is a protein with an approximate molecular weight of 240 kDa. Thus, the molar mass of the IgG-PE complex is about 390 kDa. Inserting the molar mass of the IgG-PE complex into equation (5), the diffusion coefficient for the IgG-PE complex (DIgG-PE) was calculated to be $4.0 \times 10^{-7}$ cm$^2$ s$^{-1}$. Substituting this value of the diffusion coefficient into equation (4), the radius of the IgG-PE complex (RIgG-PE) was calculated to be 5.4 nm. Inserting the radius of the IgG-PE complex value (5.4 nm), the binding rate constant $k+ = (3.1 \pm 0.4) \times 10^8$ M$^{-1}$ min$^{-1}$ (from Table 4), the valence of the ligand (2) and the valence of the receptor (1) into equation (3), the binding site radius (b) was calculated to be $1.26 \pm 0.05$.

It should be noted that the value of binding site radius b is a more convenient constant of the antigen-antibody interaction because it is independent of sizes of reagents, the type of fluorescent label and the medium properties (e.g., viscosity and temperature). The binding constant $k_+$ can be recalculated for other medium conditions, reagents and fluorescent labels using equation (3), if the value of the binding site radius b is known. Subsequently, the recalculated binding rate constant $k_+$ can be used instead of calibration for the modified system.

These studies show that, instead of using calibrators in each flow cytometry experiment, the value of the binding rate constant for a particular antibody-antigen reaction can be used in order to quantify the number of antigen molecules by flow cytometry. This approach is independent of specially prepared calibration beads and antibody reagents and can be applied to both low and high affinity antibodies, under both saturating and non-saturating binding conditions.

Example 5. Theoretical Approach for Recalculating Binding Rate Constant

In this study, recalculation of a binding rate constant was performed using a theoretical approach, which allows recalculation of a binding rate constant under differing experimental conditions (e.g., different sizes of reagent molecules, different fluorescent label, different medium viscosity and different temperature).

The value of a binding rate constant or antibody effective binding site size for a specific lot of antibody is measured once using the equation:

$$k_{\leftarrow} = N_1 N_2 \frac{k_B T b^3}{12\eta} \left(\frac{1}{R_1} + \frac{1}{R_2}\right)^3$$

where b is the radius of a circular site (so called "effective binding site" radius), which has the same rate constant of the binding, as the non-circular site considered here, $\eta$ is the viscosity of the media, kB is the Boltzmann constant, T is the temperature; $R_1$ and $R_2$ are radii, and $N_1$ and $N_2$ are valences of the first and second reactants, correspondingly. The radius of antibody molecules can be estimated from the diffusion coefficient using Stokes-Einstein equation:

$$D = \frac{k_B T}{6\pi \eta R}$$

This approach to recalculating a binding rate constant was verified by comparing the results obtained from the theoretical approach to experimentally measured binding rate constants for classical examples of monoclonal antibody-antigen pair interactions under different temperatures (Table 6) [Hy-HEL5-HEL (Xavier K A and Willson RC Biophysical Journal 1998; 74: 2036-2045); Hy-HEL5-BWQL (Xavier K A et al. Protein Eng. 1999; 12(1): 79-83); Hy-HEL10-HEL (Xavier K A and Willson RC Biophysical Journal 1998; 74: 2036-2045), D 1.3.-HEL (Ito W. et al. J. Mol. Biol. 248 (1995), pp. 729-732); 2B5-horse heart cytochrome c (Raman R et al. Biochemistry, 31 (1992), pp. 10370-10379); and 5F8-horse heart cytochrome c (Raman R et al. Biochemistry, 31 (1992), pp. 10370-10379).

TABLE 6

Comparison between binding rate constants ($k_+$) calculated by the described theoretical approach and $k_+$ calculated experimentally.

| Monoclonal antibody | Antigen | Temperature, ° C. | Water dynamic viscosity, P | $k_+$ theoretical, $M^{-1}s^{-1}$ | $k_+$ experimental, $M^{-1}s^{-1}$ |
|---|---|---|---|---|---|
| HyHEL-5 (IgG1 k) | HEL | 10 | 0.013 | $(1.6 \pm 0.2) \times 10^7$ | $(1.3 \pm 0.1) \times 10^7$ [1] |
| HyHEL-5 (IgG1 k) | HEL | 17 | 0.0108 | $(1.9 \pm 0.3) \times 10^7$ | $(1.7 \pm 0.1) \times 10^7$ [1] |
| HyHEL-5 (IgG1 k) | HEL | 32 | 0.0077 | $(2.8 \pm 0.3) \times 10^7$ | $(2.9 \pm 0.1) \times 10^7$ [1] |
| HyHEL-5 (IgG1 k) | HEL | 40 | 0.0066 | $(3.4 \pm 0.4) \times 10^7$ | $(3.9 \pm 0.2) \times 10^7$ [1] |
| HyHEL-5 (IgG1 k) | BWQL | 10 | 0.013 | $(1.2 \pm 0.3) \times 10^7$ | $(8.3 \pm 0.7) \times 10^6$ [2] |
| HyHEL-5 (IgG1 k) | BWQL | 17 | 0.0108 | $(1.4 \pm 0.3) \times 10^7$ | $(1.1 \pm 0.1) \times 10^7$ [2] |
| HyHEL-5 (IgG1 k) | BWQL | 32 | 0.0077 | $(2.1 \pm 0.5) \times 10^7$ | $(2.6 \pm 0.6) \times 10^7$ [2] |
| HyHEL-10 (IgG1 k) | HEL | 10 | 0.013 | $(3.1 \pm 0.6) \times 10^6$ | $(1.7 \pm 0.1) \times 10^6$ [1] |
| HyHEL-10 (IgG1 k) | HEL | 17 | 0.0108 | $(3.8 \pm 0.5) \times 10^6$ | $(3.0 \pm 0.4) \times 10^6$ [1] |
| HyHEL-10 (IgG1 k) | HEL | 32 | 0.0077 | $(5.7 \pm 0.7) \times 10^6$ | $(6.8 \pm 0.2) \times 10^6$ [1] |
| HyHEL-10 (IgG1 k) | HEL | 40 | 0.0066 | $(6.8 \pm 0.8) \times 10^6$ | $(9.5 \pm 0.6) \times 10^6$ [1] |
| D1.3 (Fv region) | HEL | 15.3 | 0.0114 | $(1.4 \pm 0.3) \times 10^6$ | $(1.1 \pm 0.2) \times 10^6$ [3] |
| D1.3 (Fv region) | HEL | 25.3 | 0.0089 | $(1.9 \pm 0.3) \times 10^6$ | $(1.8 \pm 0.0) \times 10^6$ [3] |
| D1.3 (Fv region) | HEL | 30 | 0.008 | $(2.1 \pm 0.4) \times 10^6$ | $(2.2 \pm 0.1) \times 10^6$ [3] |
| 2B5 (IgG2a k) | Horse heart cytochrome c | 3.8 | 0.0156 | $(3.9 \pm 0.6) \times 10^5$ | $(4.0 \pm 0.3) \times 10^5$ [4] |
| 5F8 (IgG1 k) | Horse heart cytochrome c | 3.8 | 0.0156 | $(9.1 \pm 1.2) \times 10^5$ | $(6.1 \pm 1.0) \times 10^5$ [4] |

HEL = Hen Egg Lysozyme
BWQL = Bobwhite Quail Lysozyme
[1] = Xavier KA and Willson RC Biophysical Journal 1998; 74: 2036-2045
[2] = Xavier KA et al. Protein Eng. 1999; 12(1): 79-83
[3] = Ito W. et al. J. Mol. Biol. 248 (1995), pp. 729-732
[4] = Raman R et al. Biochemistry, 31 (1992), pp. 10370-10379

Figure 8:
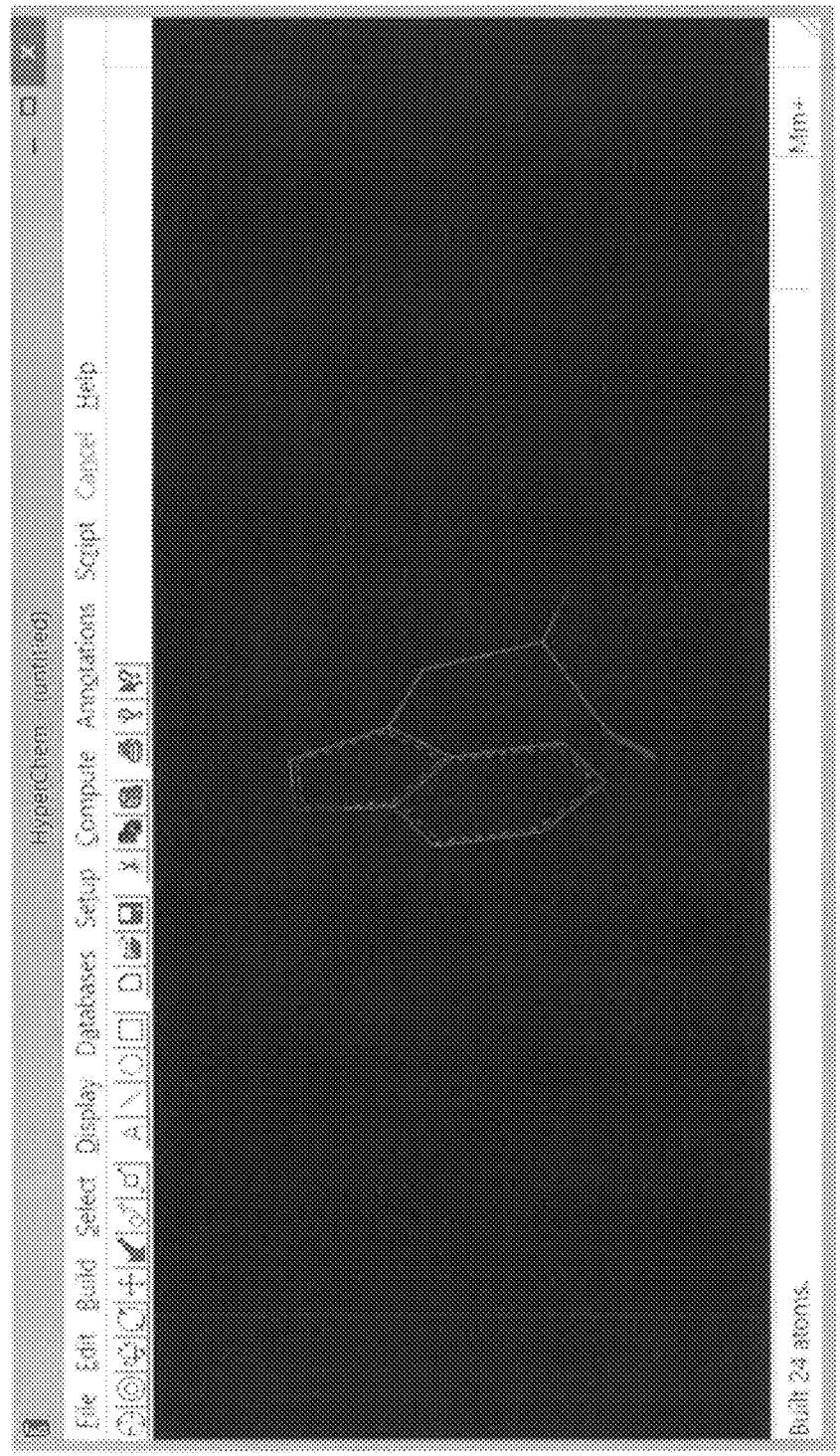
FIG. 8 shows a screenshot of HyperChem 7.5 software depicting the determination of maximum length and maximum width of dominant amino acid residues.

A theoretical approach was also employed to calculate effective binding site radius (b) using the following expression:

$$b = \frac{a}{\frac{a}{c}\ln\left(\frac{c}{a} + \sqrt{\left(\frac{c}{a}\right)^2 + 1}\right) + \ln\left(\frac{a}{c} + \sqrt{\left(\frac{a}{c}\right)^2 + 1}\right)} \quad \text{if } 1 < \frac{a}{c} < 10$$

$$b = \frac{a}{2\ln\left(2.4\frac{a}{c}\right)} \quad \text{if } \frac{a}{c} \geq 10$$

where a and c are maximum length and maximum width (assuming a>c) of dominant amino acid residues respectively (e.g. determined using HyperChem 7.5 software; FIG. 8)

This approach to calculating effective binding site radius was verified by comparing the results obtained from the theoretical approach to experimentally measured effective binding site radii (Table 7).

TABLE 7

Comparison between effective binding site radius (b) calculated by the described theoretical approach and b calculated experimentally.

| Monoclonal antibody | Anitgen | Dominant amino acid residuals from functional Ag epitope | b, effective binding site radium, nm for a-helix conformation | b, binding site radius, nm |
|---|---|---|---|---|
| HyHEL-5 (IgG1 k) | HEL | Arg45, Arg6 [5] | 0.628 | 0.564 ± 0.016 |
| HyHEL-5 (IgG1 k) | BWQL | Arg45, Lys68 [5] | 0.572 | 0.513 ± 0.028 |
| HyHEL-10 (IgG1 k) | HEL | Arg21, Asp101 [6] | 0.476 | 0.330 ± 0.009 |
| D1.3 (Fv region) | HEL | Gln121 [7] | 0.233 | 0.179 ± 0.023 |
| 2B5 (IgG2a k) | Horse heart cytochrome c | Pro44 [8] | 0.193 | 0.131 ± 0.007 |
| 5F8 (IgG1 k) | Horse heart cytochrome c | Lys60 [8] | 0.258 | 0.173 ± 0.008 |

HEL = Hen Egg Lysozyme
BWQL = Bobwhite Quail Lysozyme
[5] = Wibbenmeyer JA et al. The Journal of Biological Chemistry 1999; 274(38): 26838-26842
[6] = Kam-Morgan LNW et al. Proc. Natl. Acad. Sci. USA 1993; 90: 3958-3962
[7] = Dall'Acqua W et al. Biochemistry 1998; 37(26): 9266-9273
[8] = Pierce MM et al. METHODS 1999; 19: 213-221

For the quantification of antigen molecules with flow cytometry, the agreement between the experimental and calculated values in Tables 6 and 7 is quite satisfactory.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for quantifying a cellular antigen using flow cytometry without a calibration system, comprising:
    (a) isolating cells from a subject;
    (b) measuring concentration of the isolated cells;
    (c) mixing the isolated cells with a fluorescently-labeled antibody that specifically binds to an antigen expressed by the isolated cells to initiate an antibody-antigen binding reaction;
    (d) collecting samples of the antibody-antigen binding reaction at multiple time intervals;
    (e) stopping the antibody-antigen binding reaction in the collected samples at the time of sample collection;
    (f) analyzing the samples by flow cytometry of (e) and obtaining a measured time-series of mean fluorescence intensity (MFI); calculating reaction rate constant $k_+$ for the antibody-antigen binding reaction based on the measured time-series of mean fluorescence intensity (MFI); and calculating amount of antigen n from $k_+$, wherein the amount of antigen is quantified without a calibration system.

2. The method according to claim 1, wherein the subject is a human.

3. The method according to claim 1, wherein the cells are selected from the consisting of cytotoxic T-cells, stem cells, granulocytes, monocytes, T-lymphocytes, B-lymphocytes, thrombocytes and natural killer cells.

4. The method according to claim 3, wherein the T-lymphocytes are selected from the group consisting of cytotoxic T-cells and helper T-cells.

5. The method according to claim 4, wherein the T-lymphocytes are cytotoxic T-cells.

6. The method according to claim 1, wherein the measuring of (b) is performed by a cytometer with volumetric sample delivery.

7. The method according to claim 1, wherein the measuring of (b) is performed by a flow cytometer.

8. The method according to claim 1, wherein the fluorescently-labeled antibody is a low-affinity antibody.

9. The method according to claim 1, wherein the fluorescently-labeled antibody is a high-affinity antibody.

10. The method according to claim 1, wherein the fluorescently-labeled antibody is a phycoerythrin (PE)-labeled anti-CD8α antibody.

11. The method according to claim 1, wherein the fluorescently-labeled antibody is a fluorescein isothiocyanate (FITC)-labeled anti-CD3 antibody.

12. The method according to claim 1, wherein the stopping of (e) is performed by the addition of phosphate buffered saline (PBS) to the collected samples.

13. The method according to claim 1, further comprising calculating fluorescence signal per antibody molecule α from $k_+$.

14. The method according to claim 1, further comprising calculating antibody concentration $a_0$ from $k_+$.

15. The method according to claim 1, wherein the antibody-antigen binding reaction occurs under saturating binding conditions.

16. The method according to claim 1, wherein the antibody-antigen binding reaction occurs under non-saturating binding conditions.

17. A method for quantifying a cellular antigen using flow cytometry without a calibration system, comprising:
(a) isolating cells from a subject, wherein the cells are selected from the consisting of cytotoxic T-cells, stem cells, granulocytes, monocytes, T-lymphocytes, B-lymphocytes, thrombocytes and natural killer cells;
(b) measuring concentration of the isolated cells;
(c) mixing the isolated cells with a fluorescently-labeled antibody that specifically binds to an antigen expressed by the isolated cells to initiate an antibody-antigen binding reaction;
(d) collecting samples of the antibody-antigen binding reaction at multiple time intervals;
(e) stopping the antibody-antigen binding reaction in the collected samples at the time of sample collection;
(f) analyzing the samples by flow cytometry of (e) and obtaining a measured time-series of mean fluorescence intensity (MFI); calculating reaction rate constant $k_+$ for the antibody-antigen binding reaction based on the measured time-series of mean fluorescence intensity (MFI); and calculating amount of antigen n from $k_+$, wherein the amount of antigen is quantified without a calibration system.

* * * * *